(12) United States Patent
Moloney et al.

(10) Patent No.: US 12,161,489 B2
(45) Date of Patent: Dec. 10, 2024

(54) PACKAGING SYSTEMS AND METHODS FOR MOUNTING A TOOL ON A SURGICAL DEVICE

(71) Applicant: MAKO Surgical Corp., Weston, FL (US)

(72) Inventors: Michael Moloney, Carrick-On-Suir (IE); Seamus Gilhooley, Athenry (IE); Douglas A. Staunton, Kalamazoo, MI (US)

(73) Assignee: MAKO Surgical Corp., Weston, FL (US)

( * ) Notice: Subject to any disclaimer, the term of this patent is extended or adjusted under 35 U.S.C. 154(b) by 376 days.

(21) Appl. No.: 17/453,704

(22) Filed: Nov. 5, 2021

(65) Prior Publication Data

US 2022/0054214 A1 Feb. 24, 2022

Related U.S. Application Data

(62) Division of application No. 15/950,584, filed on Apr. 11, 2018, now Pat. No. 11,197,733.

(Continued)

(51) Int. Cl.
*A61B 50/30* (2016.01)
*A61B 17/00* (2006.01)
(Continued)

(52) U.S. Cl.
CPC .......... *A61B 50/30* (2016.02); *A61B 17/3215* (2013.01); *A61B 50/20* (2016.02);
(Continued)

(58) Field of Classification Search
CPC .... A61B 2050/0057; A61B 2050/0068; A61B 2050/0082; A61B 2050/0083;
(Continued)

(56) References Cited

U.S. PATENT DOCUMENTS

| 3,495,702 A | 2/1970 | Kuster |
|---|---|---|
| 4,260,057 A | 4/1981 | Wall-Andersen |

(Continued)

FOREIGN PATENT DOCUMENTS

| DE | 102005022385 A1 | 11/2006 |
|---|---|---|
| EP | 2298652 A1 | 3/2011 |

(Continued)

OTHER PUBLICATIONS

English language abstract for DE 10 2005 022 385 A1 extracted from espacenet.com database on May 26, 2021, 1 page.

(Continued)

*Primary Examiner* — Matthew P Travers
(74) *Attorney, Agent, or Firm* — Howard & Howard Attorneys PLLC

(57) ABSTRACT

A method for mounting a tool to a surgical device using a packaging body. A proximal section of the packaging body is articulated about a second boundary relative to a first distal section of the packaging body for removing a proximal end of the tool from a proximal cavity for exposing the proximal end. The proximal end is mounted to the surgical device while a distal end of the tool remains securely retained by first and second distal sections of the packaging body within a distal cavity. After mounting, the distal end is released from the distal cavity by articulating one distal section relative to the other distal section for exposing a first portion of the distal end that was retained by the one distal section. Thereafter, the other distal section is removed for exposing a remaining portion of the distal end that was retained by the other distal section.

13 Claims, 17 Drawing Sheets

Related U.S. Application Data

(60) Provisional application No. 62/484,547, filed on Apr. 12, 2017.

(51) Int. Cl.
| | | |
|---|---|---|
| *A61B 17/3215* | (2006.01) | |
| *A61B 50/00* | (2016.01) | |
| *A61B 50/20* | (2016.01) | |
| *B65D 17/28* | (2006.01) | |
| *B65D 75/36* | (2006.01) | |
| *A61B 34/30* | (2016.01) | |

(52) U.S. Cl.
CPC ........ *A61B 50/3001* (2016.02); *B65D 75/366* (2013.01); *A61B 2017/00526* (2013.01); *A61B 34/30* (2016.02); *A61B 2050/005* (2016.02); *A61B 2050/0057* (2016.02); *A61B 2050/0068* (2016.02); *A61B 2050/0083* (2016.02); *A61B 2050/3008* (2016.02); *A61B 2050/314* (2016.02); *B65D 17/28* (2018.01); *B65D 2575/329* (2013.01)

(58) Field of Classification Search
CPC ................ A61B 50/3001; A61B 50/30; A61B 2017/00526; B65D 17/28; B65D 17/32; B65D 75/322; B65D 2575/3227; B65D 2575/329; B65D 85/24; B65D 1/36
See application file for complete search history.

(56) References Cited

U.S. PATENT DOCUMENTS

| | | | |
|---|---|---|---|
| 4,519,501 A | | 5/1985 | Cerwin |
| 5,220,769 A | | 6/1993 | Brown et al. |
| 5,246,109 A | | 9/1993 | Markle et al. |
| 5,392,917 A | | 2/1995 | Alpern et al. |
| 5,485,917 A | | 1/1996 | Early |
| 5,542,427 A | | 8/1996 | Aekerfeldt |
| 5,542,539 A | | 8/1996 | Early |
| 5,584,164 A | | 12/1996 | Sinn |
| 5,603,318 A | | 2/1997 | Heilbrun et al. |
| 5,727,682 A | | 3/1998 | Abidin et al. |
| 5,727,685 A | | 3/1998 | Laganza et al. |
| 5,842,567 A | * | 12/1998 | Rowe ................ A61B 50/3001 206/464 |
| 5,947,288 A | | 9/1999 | Dykstra et al. |
| 6,059,111 A | | 5/2000 | Davila et al. |
| 6,059,112 A | | 5/2000 | Dykstra et al. |
| 6,161,695 A | | 12/2000 | Nicolais |
| 6,412,639 B1 | | 7/2002 | Hickey |
| 6,814,236 B2 | | 11/2004 | Roshdy |
| 6,837,027 B2 | | 1/2005 | Hickey |
| 6,915,901 B2 | | 7/2005 | Feinberg et al. |
| 7,104,401 B2 | | 9/2006 | Smith et al. |
| 7,128,208 B2 | | 10/2006 | Hull |
| 7,316,318 B1 | | 1/2008 | Rosten et al. |
| 7,320,404 B2 | | 1/2008 | Landis |
| 7,331,463 B2 | | 2/2008 | Hickey |
| 7,353,946 B2 | | 4/2008 | Cervantes |
| 7,451,870 B2 | | 11/2008 | Donahoe et al. |
| 7,467,710 B2 | | 12/2008 | Cerwin et al. |
| 7,516,845 B2 | | 4/2009 | Lang et al. |
| 7,611,008 B2 | | 11/2009 | Ruffieux et al. |
| 7,617,932 B2 | | 11/2009 | Windus-Smith et al. |
| 7,621,395 B2 | | 11/2009 | Mogensen et al. |
| 7,648,030 B2 | | 1/2010 | Landis |
| 7,726,564 B2 | | 6/2010 | Goldbach |
| 7,770,722 B2 | | 8/2010 | Donahoe et al. |
| 7,770,728 B2 | | 8/2010 | Kærn |
| 7,975,842 B2 | | 7/2011 | Thoes et al. |
| 8,006,839 B2 | | 8/2011 | Hafner |
| 8,020,703 B2 | | 9/2011 | List et al. |
| 8,042,689 B2 | | 10/2011 | Frojd et al. |
| 8,079,487 B2 | | 12/2011 | Roesler |
| D655,165 S | | 3/2012 | Jensen et al. |
| 8,146,329 B2 | | 4/2012 | Bryant et al. |
| 8,172,866 B2 | | 5/2012 | List |
| 8,261,910 B2 | | 9/2012 | Guenter et al. |
| 8,303,599 B2 | | 11/2012 | Hess et al. |
| 8,320,612 B2 | | 11/2012 | Knobel et al. |
| 8,365,910 B2 | | 2/2013 | Valaie et al. |
| 8,517,174 B2 | | 8/2013 | Dacey et al. |
| 8,770,405 B2 | | 7/2014 | Dacey et al. |
| 8,783,459 B1 | | 7/2014 | Marcinkowski |
| 8,881,900 B2 | | 11/2014 | Witt et al. |
| 8,893,883 B2 | | 11/2014 | Valaie et al. |
| 8,985,327 B2 | | 3/2015 | Roesler |
| D731,326 S | | 6/2015 | Johansson |
| 9,096,368 B2 | | 8/2015 | Wu |
| 9,138,296 B2 | | 9/2015 | Grabowski |
| 9,265,579 B2 | | 2/2016 | Richart |
| 9,474,686 B2 | | 10/2016 | Neal et al. |
| 9,532,847 B2 | | 1/2017 | Hendrickson et al. |
| 9,585,727 B2 | | 3/2017 | Richart |
| 9,592,098 B2 | | 3/2017 | Richart |
| 9,597,092 B2 | | 3/2017 | Pernot et al. |
| 9,707,039 B2 | | 7/2017 | Grabowski et al. |
| 9,717,843 B2 | | 8/2017 | Grucela et al. |
| 9,750,579 B2 | | 9/2017 | Richart |
| 9,776,783 B2 | | 10/2017 | Nadig et al. |
| 9,828,157 B2 | | 11/2017 | Roesler |
| D806,541 S | | 1/2018 | Love et al. |
| 9,872,754 B2 | | 1/2018 | Tuechsen et al. |
| 9,926,116 B2 | | 3/2018 | Kinyon |
| D818,813 S | | 5/2018 | Love et al. |
| 9,975,679 B2 | | 5/2018 | Hulliger |
| 9,999,469 B2 | | 6/2018 | Roesler |
| 10,004,567 B2 | | 6/2018 | Dacey et al. |
| 10,016,247 B2 | | 7/2018 | Grabowski et al. |
| 10,017,303 B2 | | 7/2018 | Wagner et al. |
| 10,029,043 B2 | | 7/2018 | Grucela et al. |
| 10,059,499 B2 | | 8/2018 | Roesler et al. |
| 10,086,131 B2 | | 10/2018 | Okihara |
| 10,130,439 B2 | | 11/2018 | Richart |
| 10,159,495 B1 | | 12/2018 | Lambert |
| 10,159,555 B2 | | 12/2018 | Bailly et al. |
| 2005/0218024 A1 | | 10/2005 | Lang et al. |
| 2005/0220849 A1 | | 10/2005 | Hickey |
| 2005/0251186 A1 | | 11/2005 | Revie et al. |
| 2006/0200046 A1 | | 9/2006 | Windus-Smith et al. |
| 2006/0243616 A1 | | 11/2006 | Caron |
| 2007/0203393 A1 | | 8/2007 | Stefanchik |
| 2008/0257758 A1 | * | 10/2008 | Kelly ................ A45D 33/005 206/45.24 |
| 2012/0203230 A1 | | 8/2012 | Adams |
| 2012/0305427 A1 | | 12/2012 | Felder et al. |
| 2013/0299371 A1 | | 11/2013 | Johansson |
| 2014/0163555 A1 | | 6/2014 | Pernot et al. |
| 2014/0251845 A1 | | 9/2014 | Roesler |
| 2014/0251846 A1 | | 9/2014 | Roesler |
| 2015/0196391 A1 | | 7/2015 | Dwork |
| 2015/0297296 A1 | | 10/2015 | Stauder et al. |
| 2016/0074118 A1 | | 3/2016 | Tuechsen et al. |
| 2016/0135895 A1 | | 5/2016 | Faasse et al. |
| 2016/0166350 A1 | | 6/2016 | Burkhardt et al. |
| 2016/0244234 A1 | | 8/2016 | Mayer et al. |
| 2017/0007388 A1 | | 1/2017 | Neal et al. |
| 2017/0119487 A1 | | 5/2017 | Binder et al. |
| 2017/0137194 A1 | | 5/2017 | Lorence |
| 2017/0290634 A1 | | 10/2017 | Dacey |
| 2017/0340401 A1 | * | 11/2017 | Miller ................ A61B 50/30 |
| 2017/0349347 A1 | | 12/2017 | Bentz |
| 2017/0355505 A1 | | 12/2017 | Nadig et al. |
| 2018/0162619 A1 | | 6/2018 | Kocur et al. |
| 2018/0222655 A1 | | 8/2018 | Grabowski et al. |
| 2018/0235348 A1 | | 8/2018 | Booker |
| 2018/0296293 A1 | | 10/2018 | Ueda |
| 2018/0296297 A1 | | 10/2018 | Moloney et al. |
| 2018/0296749 A1 | | 10/2018 | Grucela et al. |
| 2018/0311008 A1 | | 11/2018 | Grabowski et al. |
| 2018/0344422 A1 | | 12/2018 | Deck |
| 2019/0001050 A1 | | 1/2019 | Okihara |

(56) References Cited

U.S. PATENT DOCUMENTS

| | | |
|---|---|---|
| 2019/0315563 A1 | 10/2019 | Johansson |
| 2020/0054199 A1 | 2/2020 | Kambe et al. |
| 2020/0383746 A1 | 12/2020 | Moloney et al. |

FOREIGN PATENT DOCUMENTS

| | | |
|---|---|---|
| EP | 2292528 B1 | 2/2013 |
| EP | 2662312 B1 | 10/2014 |
| GB | 2584534 A | 12/2020 |
| WO | 2011135246 A2 | 11/2011 |
| WO | 2017087732 A1 | 5/2017 |
| WO | 2017129757 A1 | 8/2017 |
| WO | 2017176569 A1 | 10/2017 |
| WO | 2017185029 A1 | 10/2017 |
| WO | 2017185052 A1 | 10/2017 |
| WO | 2018011257 A1 | 1/2018 |
| WO | 2018052832 A1 | 3/2018 |
| WO | 2018106110 A1 | 6/2018 |
| WO | 2018112107 A1 | 6/2018 |
| WO | 2018156589 A2 | 8/2018 |
| WO | 2018156611 A1 | 8/2018 |
| WO | 2018164497 A1 | 9/2018 |
| WO | 2018198308 A1 | 11/2018 |
| WO | 2018202805 A1 | 11/2018 |
| WO | 2018227066 A1 | 12/2018 |
| WO | 2019035096 A1 | 2/2019 |

OTHER PUBLICATIONS

English language abstract for WO 2011/135246 extracted from espacenet.com database on Jul. 8, 2020, 2 pages.

English language abstract and machine-assisted English translation for WO 2018/164497 extracted from espacenet.com database on Apr. 16, 2020, 15 pages.

English language abstract for WO 2018/198308 extracted from espacenet.com database on Apr. 16, 2020, 2 pages.

English language abstract and machine-assisted English translation for WO 2018/202805 extracted from espacenet.com database on Apr. 16, 2020, 14 pages.

International Search Report for Application No. PCT/US2018/027138 dated Jun. 25, 2018, 3 pages.

English language abstract for EP 2 292 528 extracted from espacenet.com database on Feb. 27, 2020, 1 page.

\* cited by examiner

PACKAGING SYSTEMS AND METHODS FOR MOUNTING A TOOL ON A SURGICAL DEVICE

CROSS REFERENCE TO RELATED APPLICATIONS

The subject application is a Division of U.S. Non-Provisional patent application Ser. No. 15/950,584, filed on Apr. 11, 2018, which claims priority to and all benefits of U.S. Provisional Patent App. No. 62/484,547, filed on Apr. 12, 2017, the contents of each of the aforementioned applications being hereby incorporated by reference in their entirety.

BACKGROUND

A surgical device such as a robot often receives a tool or instrument for use during a surgical procedure. The tool may be a cutting accessory, such as a bur or drill, having a head with sharp features configured to resect tissue such as bone. Suboptimal packaging and handling of the tool may result in surgical site infection, injury, and other undesirable consequences.

Surgical site infections (SSIs) are one of the most commonly identified types of healthcare associated infections. The SSIs relevant to the present disclosure result from contamination of the tool with infectious material during handling and mounting of the tool on the surgical device. Known methods may include a user, such as an operating room technician, removing the tool from packaging and placing it on a table until it is necessary to mount the tool on the surgical device. The tool may be placed in intermediate packaging such as a poly bag, after which the user removes the tool from the poly bag for mounting on the surgical device. The known methods require the tool be physically handled by the user after removal from the packaging or intermediate packaging. For an elongate tool having a shaft coupled to the head, the shaft is mounted on the surgical device and requires the user to handle the tool proximate the head and its sharp features. It is well documented that hand hygiene is not always correctly performed, and proper hand hygiene may not always remove all pathogenic organisms. The inadvertent transference of pathogenic organisms from the user to the tool increases the risk of SSIs.

Known packaging also may not adequately prevent contact between the sharp features of the cutting accessory and the packaging during handling and removal of the tool. The user may, for example, pluck the shaft of the tool from the packaging. Should the head of the cutting accessory contact the packaging body during handling or removal, the sharp features may shave or otherwise remove small bits of the packaging. The bits may be imperceptible and remain on the head of the cutting accessory after being mounted on the surgical device. The bits may be introduced to the patient during the surgical procedure and increase the risk of SSIs from the body's response to the foreign material.

Often with surgical devices comprising a robot, the tool is mounted to the robot in advance of its use during the surgical procedure. In the interim, the head of the tool and its sharp features remain exposed in an unprotected manner for some time up to the point of use. The unprotected tool is associated with risk of contamination and/or injury, particularly as a surgical team moves about the operating room. For example, the operating room technician may inadvertently bump into the tool causing contamination of the tool, injury to the technician, and/or damage to the surgical device.

Furthermore, providing suitable packaging for surgical tools may require one or more components with intricate features that are costly to manufacture. The complexity and costs of the manufacturing and assembly processes may be further influenced by regulatory requirements and industry standards.

Packaging systems and methods designed to overcome one or more of the aforementioned disadvantages is desired.

SUMMARY

A method for mounting an elongate tool to a surgical device using a segmented packaging body, the elongate tool comprising a distal end and a proximal end, and the segmented packaging body comprising a first distal section, a second distal section pivotably coupled to the first distal section at a first boundary, and a proximal section pivotably coupled to the first distal section at a second boundary, wherein the first and the second distal sections are removably attached to one another to securely retain the distal end of the elongate tool within a distal cavity collectively formed by the first and the second distal sections, and the proximal end of the elongate tool is disposed within a proximal cavity formed by the proximal section, the method comprising: articulating the proximal section about the second boundary relative to the first distal section for removing the proximal end of the elongate tool from the proximal cavity for exposing the proximal end; after exposing the proximal end, mounting the proximal end to the surgical device while the distal end remains securely retained by the first and second distal sections within the distal cavity; after mounting the proximal end to the surgical device, releasing the distal end of the elongate tool from the distal cavity by: articulating one of the first and second distal sections about the first boundary relative to the other one of the first and second distal sections for exposing a first portion of the distal end that was retained by the one of the first and second distal sections; and removing the other one of first and second distal sections from the distal end for exposing a remaining portion of the distal end that was retained by the other one of the first and second distal sections.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

Figure 1:
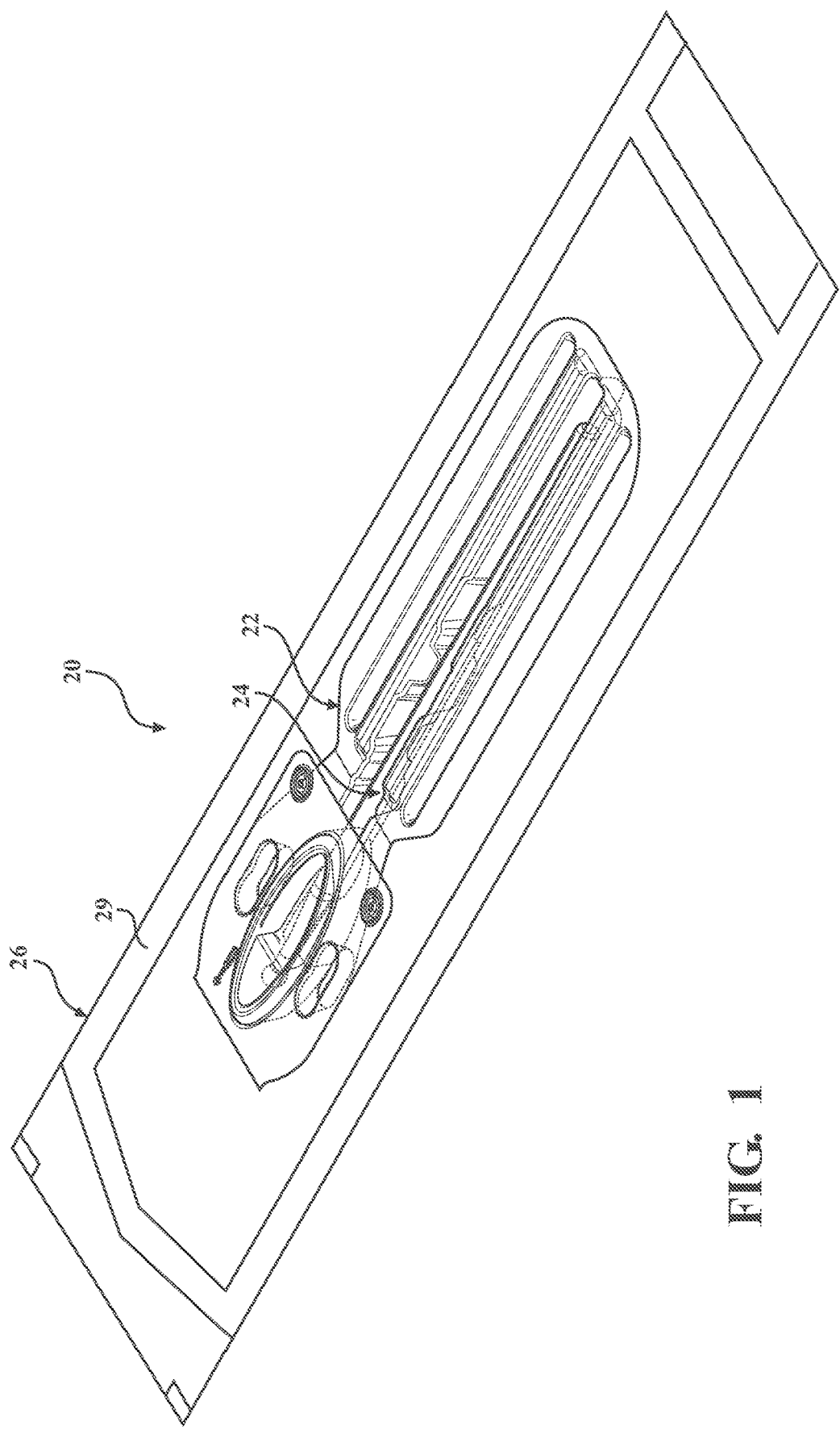
FIG. 1 is a perspective view of a packaging system in accordance with an exemplary embodiment of the present disclosure.

FIG. 1 shows a packaging system 20 according to one exemplary embodiment. The packaging system 20 comprises a segmented packaging body 22 configured to removably receive an elongate tool 24. Secondary packaging 26 may be provided and configured to receive the packaging body 22. In the embodiment illustrated in FIG. 1, the secondary packaging 26 comprises a sealed pouch having opposing layers coupled through, for example, heat sealing, adhesive, and the like. The seal 29 may extend around the packaging body 22 once disposed between the layers to provide a hermetic seal. The layers of the secondary packaging 26 may be peeled apart to expose the packaging body 22 for functions to be disclosed.

The secondary packaging 26 may comprise a blister pack. A tray with a cavity is formed within a suitable material, preferably thermoformed plastic. The cavity may be formed in a suitable geometry to accommodate the packaging body 22. A film is removably attached about a periphery of the formed tray to provide a peel-open feature. The film may be porous to allow sterilization. One suitable film is Tyvek® manufactured by DuPont™ (Wilmington, Del.). In another example, the film may be applied directly to the packaging body 22. In such an example, the film provides supplemental security for the tool 24 within the packaging body 22. Other types of secondary packaging are contemplated, but it is to be understood the packaging systems described herein may comprise the packaging body without secondary packaging.

Figure 2:
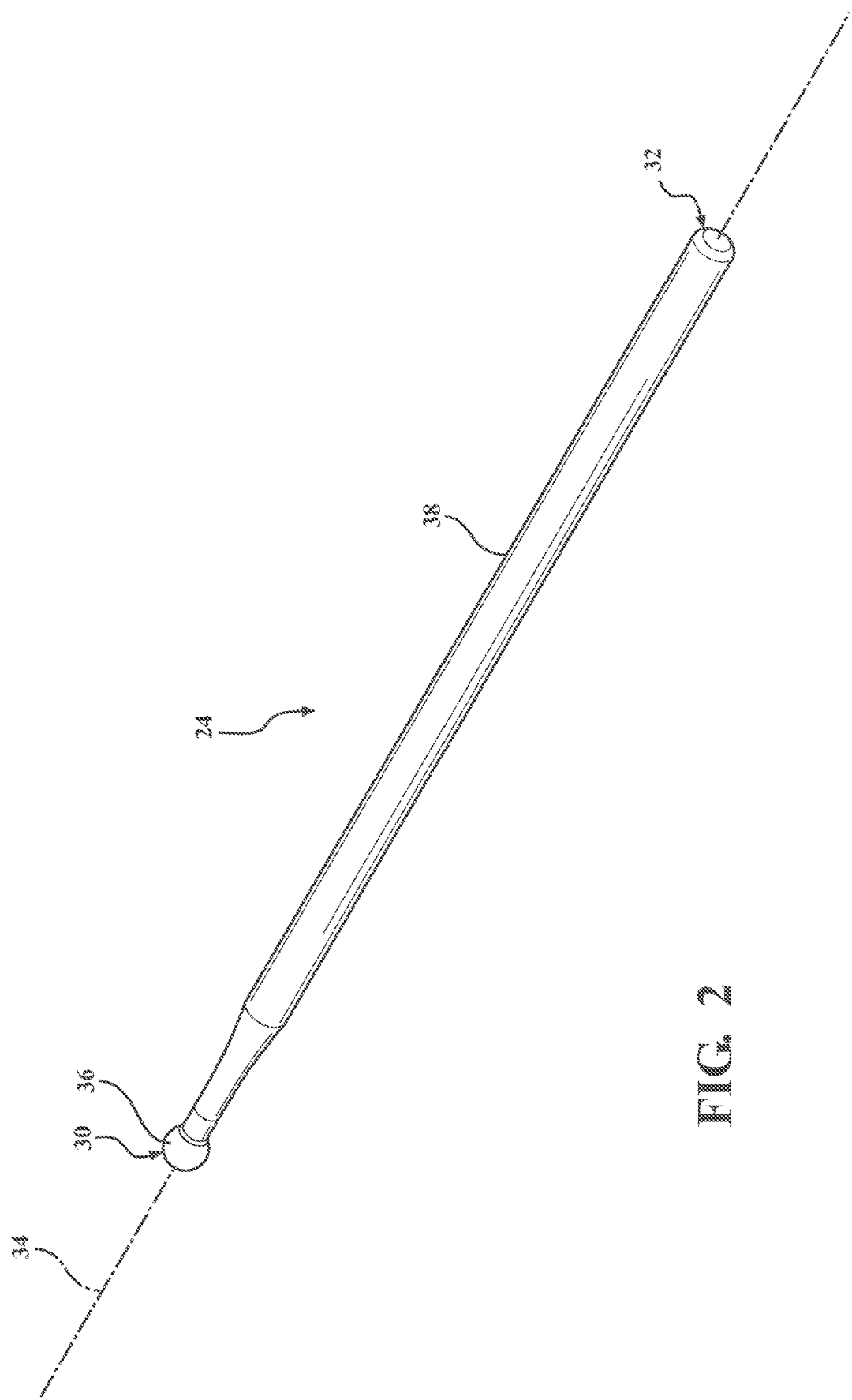
FIG. 2 is a perspective view of an elongate tool.
Figure 11:
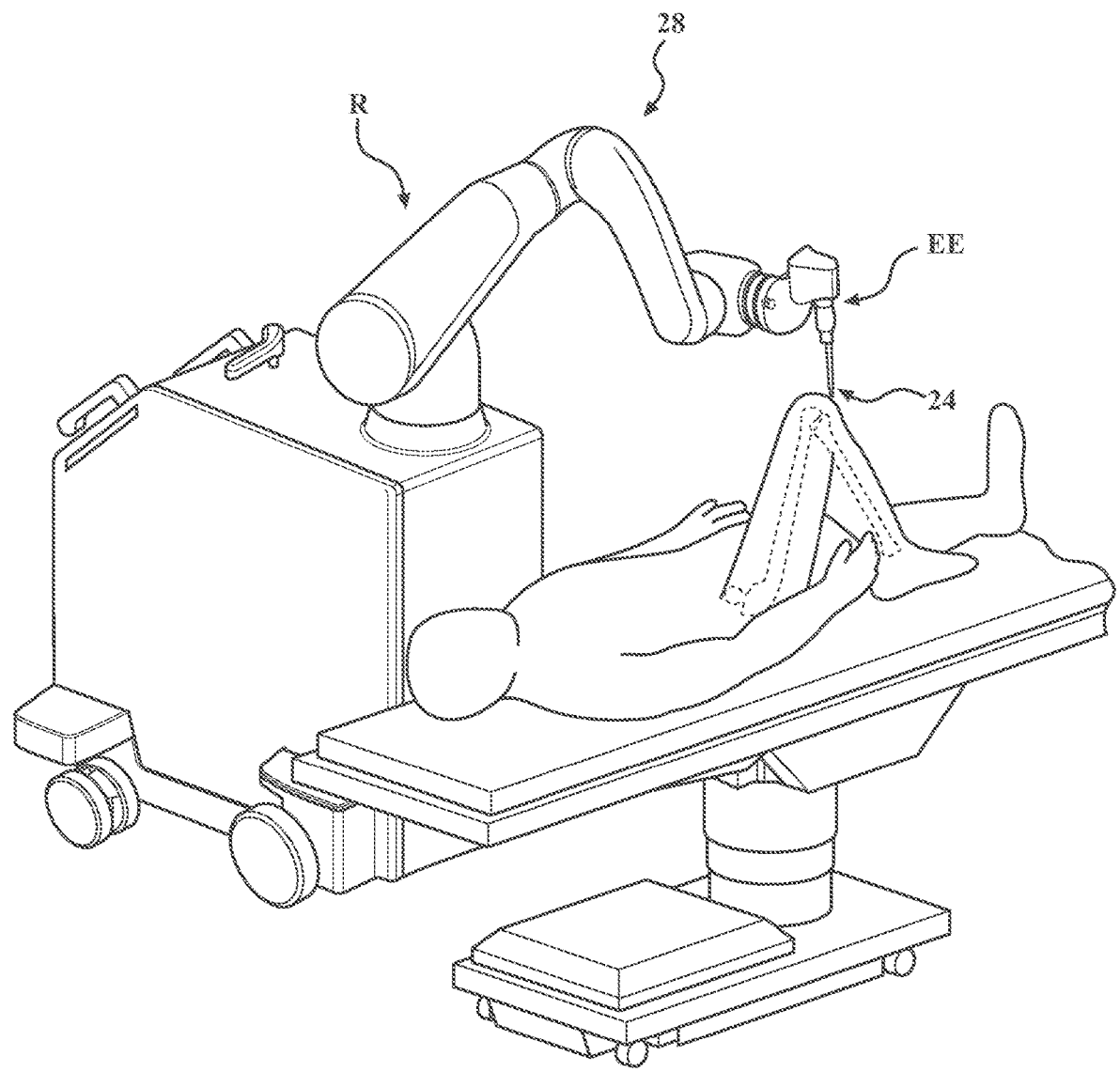
FIG. 11 is a surgical device.

The packaging system 20 provides safe, sterile and secure handling of the tool 24 during storage, transport, and mounting of the tool 24 on a surgical device 28 (see FIG. 11). FIG. 2 shows an exemplary tool for use with the packaging systems described herein. The tool 24 comprises a distal end 30 and a proximal end 32 opposite the distal end 30. A length of the tool 24 is defined between the distal end 30 and the proximal end 32. A tool axis 34 may be defined between the distal end 30 and the proximal end 32. A width of the tool 24 is less than the length such that the tool 24 may be defined as elongate. The tool 24 of FIG. 2 is circular in cross section, but it is to be understood that other suitable shapes are contemplated, including triangles, squares, and higher order polygons. The tool could be curved or a non-linear elongated device, or it could be a movable multi-piece assembly. Other types of surgical tools are contemplated.

The proximal end 32 is configured to be coupled to the surgical device 28. The surgical device 28 may be any apparatus configured to receive the tool 24. The tool 24 may be the instrument that directly interfaces with the patient, whereas the surgical device 28 may provide actuation, control, power, and the like to the tool 24. The surgical device 28 of FIG. 11 is a surgical robot R having an end effector EE configured to receive the tool 24. In certain embodiments, the tool 24 is a resection instrument such as a surgical bur or drill. FIG. 2 shows the surgical bur with the distal end 30 comprising a head 36 with the head 36 rigidly coupled to a shaft 38 extending to the distal end 32. Exemplary surgical burs include the CORE™ Burs manufactured by Stryker® Corporation (Kalamazoo, Mich.).

Other examples of the tool 24 and the surgical device 28 configured to receive the tool 24 are contemplated. For example, possible combinations of the tool 24 and the surgical device 28 may comprise: a router, a curved bur, or a sleeve connector for a bur configured to be received by a handheld rotary instrument; electrodes configured to be received by a smoke evacuation pencil; a saw or a blade configured to be received by a saw driver; a scalpel configured to be received by a scalpel handle; an ultrasonic tip configured to be received by a sonopet; and an endoscopic shaver or cutter configured to be received by an endo-handpiece. It is to be understood that other surgical devices for receiving tools are contemplated.

A cutting accessory sleeve (not shown) or collet may be provided and disposed about the shaft 38. The packaging body 22 may be suitably shaped to accommodate the tool 24 with or without the cutting accessory sleeve coupled to the shaft 38. Receiving the cutting accessory sleeve within the packaging body 22 may facilitate improved mounting of the tool 24 on the surgical device 28 in manners to be described.

Figure 3:
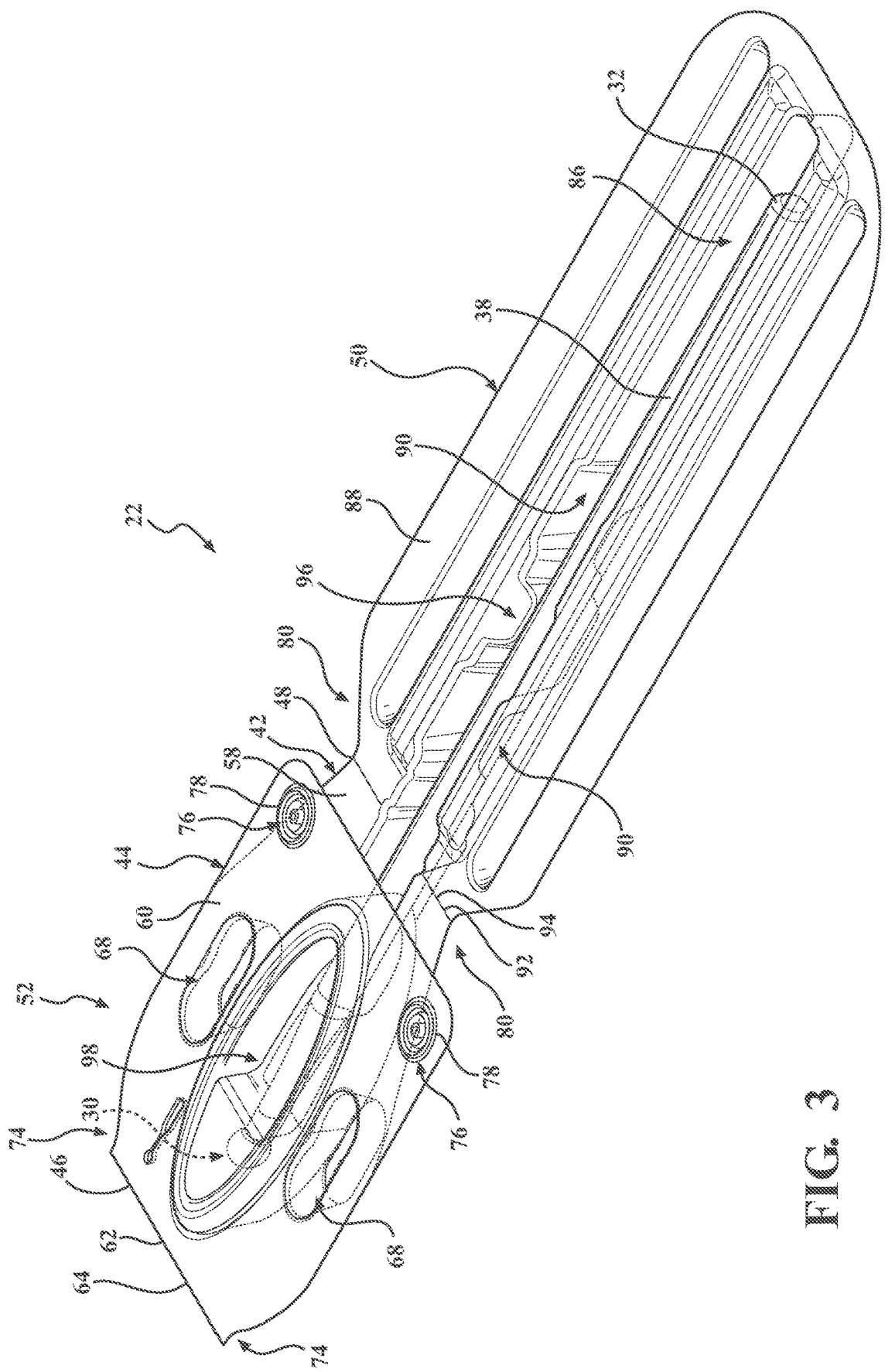
FIG. 3 is a perspective view of a packaging body in accordance with an exemplary embodiment of the present disclosure with an elongate tool disposed within the packaging body in a first configuration.
Figure 4:
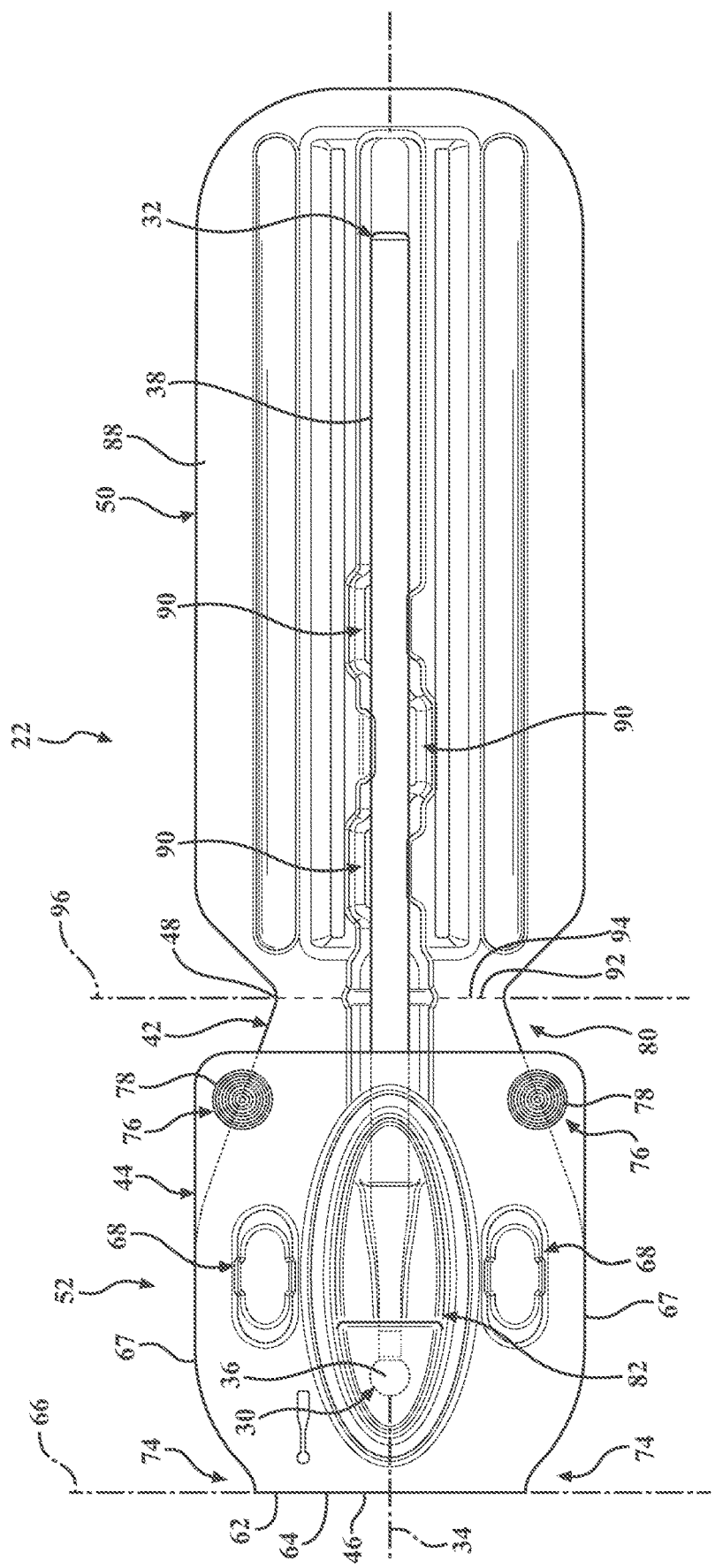
FIG. 4 is a top plan view of the packaging body of FIG. 3.
Figure 5:
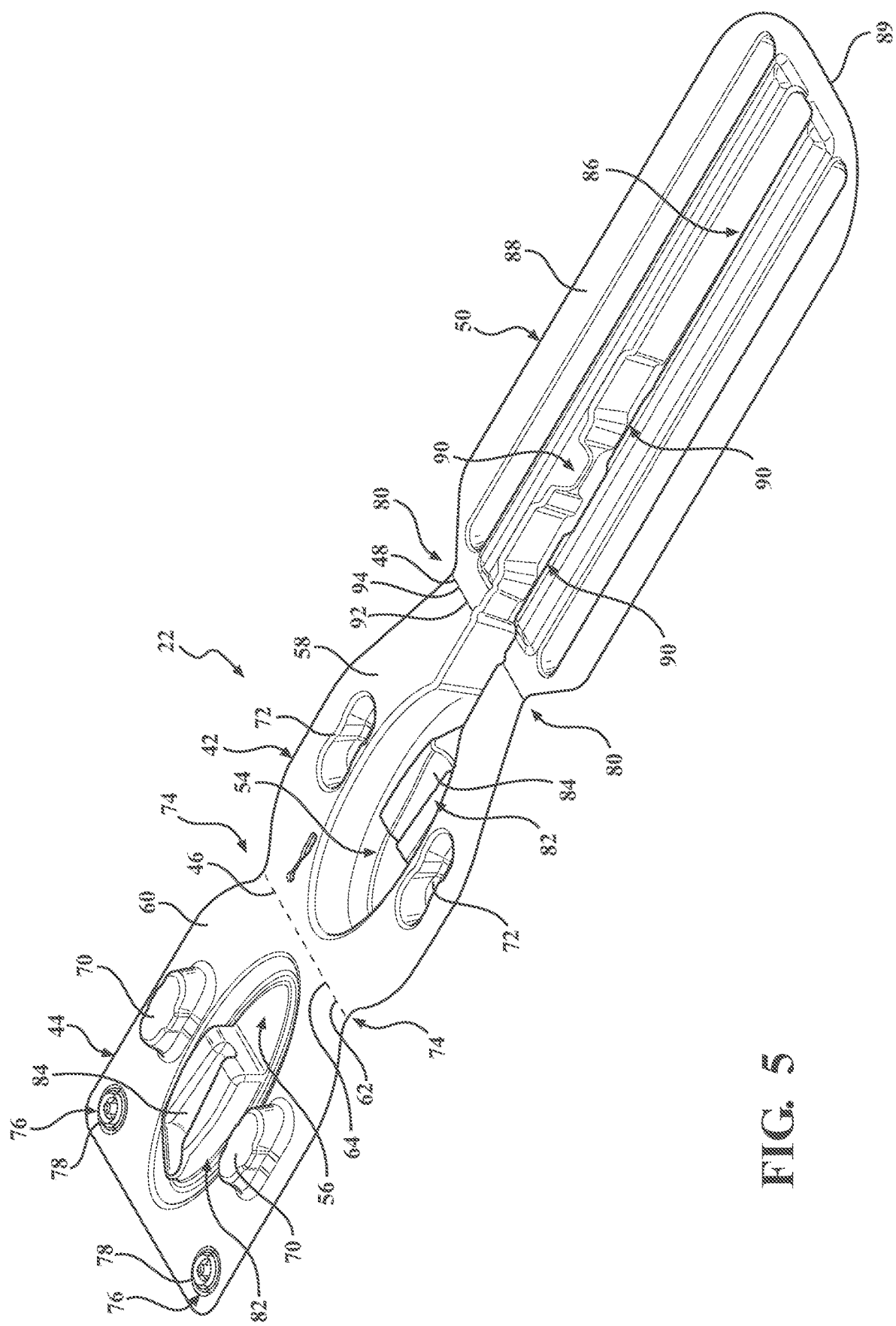
FIG. 5 is a perspective view of the packaging body of FIG. 3 in a second configuration with the elongate tool removed from the packaging body.

Referring to FIGS. 3-5, the segmented packaging body 22 of the present embodiment of the packaging system 20 is shown. The packaging body 22 comprises a first distal section 42 and a second distal section 44. The first distal section 42 comprises a first boundary and a second boundary. In some embodiments, the boundaries comprise a distal boundary 46 and a proximal boundary 48. The second distal section 44 is coupled to the first distal section 42 at the distal boundary 46. The packaging body 22 further comprises a proximal section 50 coupled to the first distal section 42 at the proximal boundary 48. The packaging body may be comprised in part or entirely of polyethylene terephthalate glycol-modified (PETG). Other suitable materials may include, without limitation, polymers such as polyethylene terephthalate (PET), high-density polyethylene (HDPE), polyvinyl chloride (PVC), low-density polyethylene (LDPE), polypropylene (PP), and polystyrene (PS), epoxy and other resins, and malleable metals such as aluminum. The packaging body 22 is preferably formed by thermoforming, but injection molding, vacuum molding, blow molding, and other manufacturing processes are also contemplated.

The first and second distal sections 42, 44 are configured to receive the distal end 30 of the tool 24. FIGS. 3 and 4 show the first and second distal sections 42, 44 receiving the distal end 30 and a portion of the shaft 38 of the tool 24. The first and second distal sections 42, 44 may be pivotally coupled to provide a clamshell casing 52 to the distal end 30 of the tool 24.

The clamshell casing 52 may be provided by a cavity 54, 56 disposed in each of the first and second distal sections 42, 44. With reference to FIGS. 3 and 5, the first distal section 42 comprises a primary surface 58 extending between the distal boundary 46 and the proximal boundary 48. The cavity 54 may be disposed within the primary surface 58 and positioned intermediate the distal boundary 46 and the proximal boundary 48. The second distal section 44 comprises a primary surface 60 with the cavity 56 disposed within the primary surface 60. The primary surfaces 58, 60 may be considered as substantially flat portions of first and second distal sections 42, 44 to which many of the features described herein are formed or otherwise coupled. The cavities 54, 56 of each of the first and second distal sections 42, 44 may be in substantial alignment so as to receive the distal end 30 of the tool 24 in a first configuration to be described. In other embodiments, only one of first and second distal sections 42, 44 may comprise a cavity suitably dimensioned to receive the distal end 30 of the tool 24 with the other one of first and second distal sections 42, 44 being substantially flat. In certain embodiments, the proximal section 50 may comprise a flat surface devoid of the cavity 86. In such an example, the flat surface may extend adjacent to the shaft 38 of the tool 24.

The clamshell casing 52 may be provided by articulating one of the first and second distal sections 42, 44 relative to the other to the first configuration shown in FIGS. 3 and 4. The second distal section 44 may be pivotally coupled to the first distal section 42 at the distal boundary 46. In certain embodiments, the second distal section 44 is pivotally coupled to the first distal section 42 about an axis 66 perpendicular to the tool axis 34 of the tool 24. In certain embodiments, the tool 24 may be curved, such as a curved portion extending distally from a straight portion. In such an embodiment, the clamshell casing 52 may be generally arcuate in shape. Alternatively, the packaging may be oriented similar to that shown in FIG. 4, but otherwise configured to accommodate the curved tool.

In one example, the packaging body 22 comprises a living hinge 62 at the distal boundary 46. The living hinge 62 may be described as a thin, flexible connection or web coupling first and second distal sections 42, 44. The living hinge 62 may be a consequence, at least in part, of perforations 64 at the distal boundary 46. In some cases, the first distal section 42 may be configured to be detachable from the second distal section 44 at the perforations 64. Other suitable ways of effectuating relative movement between the first and second distal sections 42, 44 are contemplated. For example, a flexible material may couple the first and second distal sections 42, 44 and/or may couple the first distal section 42 and the proximal section 50. In such an embodiment, the first and second distal sections 42, 44 and the proximal section 50 are discrete structures coupled by the material adapted to bend so as to enable the relative pivoting at the distal boundary 46 and/or the proximal boundary 48. In one example, the flexible material comprises an adhesive adapted to join an adjacent two of the sections 42, 44, 50. A portion of the flexible material is adhered to each of the adjacent two of the sections 42, 44, 50 with or without a small gap disposed between the adjacent two of the sections 42, 44, 50. If desired, the adjacent two of the sections 42, 44, 50 may be separated by providing sufficient force to overcome the adhesive force.

The second distal section 44, for example, may be pivoted relative to the first distal section 42 to provide the clamshell casing 52. In other words, at least one of the first and second distal sections 42, 44 is configured to move between the first configuration and a second configuration. In the second configuration to be described in greater detail, the first and second distal sections 42, 44 are positioned in a non-abutting relationship. In the first configuration, the first and second distal sections 42, 44 are positioned in an abutting relationship such that the distal end 30 of the tool 24 is encased between the first and second distal sections 42, 44. In the exemplary embodiment shown in FIGS. 4 and 5, the second distal section 44 may be moved or folded over onto the first distal section 42 such that the primary surfaces 58, 60 are in a direct abutting relationship. The movement is guided by the living hinge 62 oriented on the axis 66 such that the first and second distal sections 42, 44 are generally aligned atop one another in the first configuration. The direct abutting relationship of the primary surfaces 58, 60 provides the clamshell casing 52 to the distal end 30 of the tool 24. In the first configuration, the primary surfaces of the first and second distal sections 42, 44 are substantially parallel.

In certain embodiments, including those illustrated throughout the present disclosure, the distal boundary 46 is opposite the proximal boundary 48 such that in the second configuration, the first and second sections 42, 44 and the proximal section 50 are generally aligned or positioned in-line, as illustrated in FIG. 5. In other words, in the second configuration with the primary surfaces 58, 60 of the first and second distal sections 42, 44 positioned in a non-abutting relationship, the first distal section 42 is positioned adjacent the second distal section 44 opposite the proximal section 50. Certain modifications of the packaging body 22 are contemplated. For example, one of the lateral edges 67 (see FIG. 4) may comprise the living hinge 62 about which one of the first and second distal sections 42, 44 is configured to move between the first configuration and the second configuration. In such an example, the first and second distal sections 42, 44 are pivotally coupled at a side boundary and not at the distal boundary 46. The function of the clamshell casing 52 is substantially as described with the relative pivoting about one of the lateral edges 67 resulting in the sections 42, 44, 50 assuming an L-shaped configuration.

The packaging body 22 further comprises couplers 68 removably coupling the first and second distal sections 42, 44. The couplers 68 are configured to maintain the first and second distal sections 42, 44 in the first configuration absent an input from a user to be described. The couplers 68 may operate by interference or friction fit, but other modes of securing the first and second distal sections 42, 44 are contemplated, such as adhesive. In certain embodiments, the couplers 68 comprise a protrusion 70 removably coupled to a recess 72 by interference fit in the first configuration. More specifically, the recess 72 may be provided within one of the first and second distal sections 42, 44, and the protrusion 70 provided on the other one of the first and second distal sections 42, 44. In the exemplary embodiment shown in FIGS. 3-5, two recesses 72 are provided within the first distal section 42, and two protrusions 70 provided on the second distal section 44. The protrusions 70 and recesses 72 are positioned on opposing sides of the cavities 54, 56 of the first and second distal sections 42, 44, respectively. The protrusion 70 and the recess 72 may extend from the primary surfaces 58, 60 of the first and second distal sections 42, 44. The interference fit between the protrusion 70 and the recess 72 maintains the clamshell casing 52 such that the first and second distal sections 42, 44 encase the distal end 30 of the tool 24. Additionally or alternatively, additional structures may be formed within the cavities 54, 56 to create an interference fit between the first and second distal sections 42, 44 to maintain the clamshell casing 52 in the first configuration. In other exemplary embodiments, one of the first and second distal sections 42, 44 may comprise edges with a "folded" or "crimped" shape so as to create the interference fit (or snap-fit) with edges of the other one of the first and second distal sections 42, 44. For example, the lateral edges 67 of the second distal section 44 may be formed such that the lateral edges 67 deflect when moving the clamshell casing 52 of the packaging body 22 between the first and second configurations. The clamshell casing 52 provides, among other advantages to be described, secure handling of the distal end 30 of the tool 24.

The second configuration provides positioning the first and second distal sections 42, 44 in the non-abutting relationship, thereby exposing a portion of the distal end 30 of the tool 24 disposed within the first distal section 42. FIG. 5 shows the second configuration (with the tool 24 removed). Positioning the packaging body 22 in the second configuration typically occurs after the tool 24 is mounted on the surgical device 28 in a manner to be described. Moving the packaging body 22 from the first configuration to the second configuration comprises pivoting one of the first and second distal sections 42, 44 relative to the other. In one example, one of the first and second distal sections 42, 44 is pivoted about the distal boundary 46 comprising the living hinge 62 oriented on the axis 66 transverse to the tool axis 34. The desired movement may be further facilitated by cutouts 74 disposed at opposing ends of the distal boundary 46. The cutouts 74 comprise material removed or absent from one or more of the first and second distal sections 42, 44 at the opposing ends of the distal boundary 46, as shown in FIGS. 3-5. The cutouts 74 may comprise material removed or absent from one or more of the first distal section 42 and the second distal section 44 at a singular one of the opposing ends of the distal boundary 46. The cutouts 74 of the illustrative embodiment are generally triangular when viewed in plan, but other suitable shapes are contemplated. The cutouts 74 may localize stresses at the opposing ends of the distal boundary 46 to facilitate relative pivoting of first and second distal sections 42, 44 at the distal boundary 46.

The relative pivoting is typically imparted by the user holding the packaging body 22. In one example, the user may hold the proximal section 50 and/or the first distal section 42 in one hand and grasp the second distal section 44 with the other hand in order to overcome the interference fit of the couplers 68. The user may use fingers to pinch or grasp the second distal section 44 while holding the first distal section 42. The packaging body 22 may further comprise a finger grip 76 configured to be grasped by the fingers of the user. The second distal section 44 comprises the finger grip 76 positioned and/or extending outwardly from the first distal section 42. FIGS. 3-5 show two finger grips 76 positioned on opposite sides of the cavity 56. In certain embodiments, the finger grip 76 may comprise a portion of the primary surface 60 of the second distal section 44 extending outwardly from the first distal section 42. The portion of the primary surface 60 may be positioned adjacent and/or proximate to cutouts 80 associated with the proximal boundary 48 for functions to be described. The finger grip 76 in combination with the cutouts 80 provides a suitable surface to facilitate disengagement of the interference fit of the couplers 68. In certain embodiments, the finger grip 76 is the portion of the primary surface 60 of the second distal section 44 to be grasped by the user to apply a force to disengage the protrusion 70 from the recess 72, thereby initiating the relative pivoting of the first and second distal sections 42, 44. Additionally or alternatively, the finger grip 76 may comprise a texturized feature 78 configured to be grasped between the fingers of the user. The texturized feature 78 further provides a gap between the first and second distal sections 42, 44 with the gap adapted to be engaged by one of the fingers of the user. In certain embodiments, material of durable strength, such as a string, may be provided and rigidly coupled to one of the first and second distal sections 42, 44. The material is adapted to be grasped by the user to facilitate moving the clamshell casing 52 from the first configuration to the second configuration. In another exemplary embodiment, a portion of the second distal section 44 may include a tab of elevated material to be pinched between the fingers of the user to facilitate moving the clamshell casing 52 from the first configuration to the second configuration.

The clamshell casing 52 may comprise features configured to prevent contact of the head 36 of the tool 24 with the first and second distal sections 42, 44 when the tool 24 is secured within the packaging body 22. Each of the first and second distal sections 42, 44 may comprise a boss 82 configured to support the tool 24 proximate the distal end 30. Referring to FIG. 5, the boss 82 is disposed within the cavities 54, 56 of each of the first and second distal sections 42, 44. The boss 82 may extend from a base surface partially defining the cavity. The boss 82 may comprise a slot 84 flanked by ridges with the slot 84 configured to receive the shaft 38 of the tool 24 proximal the head 36. The ridges are suitably sized such that when the couplers 68 are coupled in the first configuration, the shaft 38 of the tool 24 proximal the head 36 is securely encircled within the slots 84. The clamshell casing 52 may be considered substantially contoured to the distal end 30 of the tool 24. The head 36 of the tool 24 is distal the boss 82, as shown in FIG. 4, and suspended with the clamshell casing 52. In other words, the head 36 of the tool 24 is spaced at a distance from surfaces of the packaging body 22 to prevent contamination of the tool 24. In one example, eight millimeters of clearance is provided about the head 36 of the tool 24. In other examples, four, six or ten or more millimeters of clearance may be provided. During mounting or installation of the tool 24 with the surgical device 28 as to be described, the user may grasp the clamshell casing 52 without risk of touching the tool 24 and without contamination of the tool 24 from the packaging body 22.

The packaging body 22 comprises the proximal section 50 coupled to the first distal section 42 at the proximal boundary 48. The proximal section 50 may further comprise a primary surface 88 coupled to the primary surface 58 of the first distal section 42 at the proximal boundary 88. The primary surface 88 may be considered as substantially flat portions of proximal section 50 to which many of the features described herein may be formed or otherwise coupled. The proximal section 50 is configured to receive the proximal end 32 of the tool 24. Referring to FIGS. 3 and 4, the proximal section 50 receives a proximal portion of the shaft 38 of the tool 24 comprising the proximal end 32. The proximal section 50 comprises a cavity 86 configured to receive the proximal portion of the tool 24. In certain embodiments, the cavity 86 is disposed within the primary surface 88 and positioned intermediate the proximal boundary 48 and a proximal edge 89 of the packaging body 22. FIGS. 3-5 show the cavity 86 is an elongate cavity and suitably sized to receive the tool 24.

The tool 24 may be secured within the cavity 86 with one or more shaft couplers 90. The shaft couplers 90 may comprise a protrusion with a counterposing recess. The protrusion may extend into the cavity 86 with the counterposing recess extending outwardly from the cavity 86 opposite the protrusion. The arrangement of the shaft coupler 90 provides an interference fit to the shaft 38 of the tool 24. Based on the material composition and thickness of the packaging body 22, a small amount of elastic deformation of the shaft coupler 90 occurs as the tool 24 is urged within the cavity 86 of the proximal section 50. Once received within the cavity 86 the protrusion of the shaft coupler 90 positioned superior the tool 24 returns to a natural state and provides the interference fit for the shaft 38 of the tool 24. FIGS. 3-5 show three shaft couplers 90 spaced axially along the cavity 86 of the proximal section 50, but one, two, four or more shaft couplers are contemplated. Each of the three shaft couplers 90 is arranged in an opposite manner from an adjacent shaft coupler 90. In other words, the protrusion and the counterposing recess of one shaft coupler 90 are "flipped" relative to the adjacent shaft coupler 90. The resulting arrangement provides the interference fit on radially opposite positions on the shaft 38 for improved retention of the tool 24 within the proximal section 50.

The cavities 54, 56, 86 of the first and second distal sections 42, 44 and the proximal section 50 are configured to receive a portion of the tool 24. The cavity 54 of the first distal section 42 and the cavity 86 of the proximal section 50 may be substantially collinear. In embodiments where the shaft 38 of the tool 24 is cylindrical and rigid, the cavities 54, 86 receiving a portion of the shaft 38 are substantially collinear or aligned to receiving the tool 24 within the packaging body 22. FIGS. 3-5 show the cavity 54 of the first distal section 42 and the cavity 86 of the proximal section 50 being continuous such that each of the cavities 54, 86 extend to the proximal boundary 48 and form a singular channel between the first distal section 42 and the proximal section 50.

The proximal section 50 may be pivotally coupled to the first distal section 42 at the proximal boundary 48. FIGS. 3-5 show the primary surface 58 of the first distal section 42 pivotally coupled to the primary surface 88 of the proximal section 50 at the proximal boundary 48. The packaging body 22 may further comprising a living hinge 92 at the proximal boundary 48 configured to facilitate pivoting the proximal section 50 relative to the first distal section 42. The living hinge 92 may be described as a thin, flexible connection or web coupling first distal section 42 and the proximal section 50, and more particularly the primary surfaces 58, 88. The living hinge 92 may be a consequence, at least in part, of a perforation 94 at the proximal boundary 48 for functions to be described.

Figure 6:
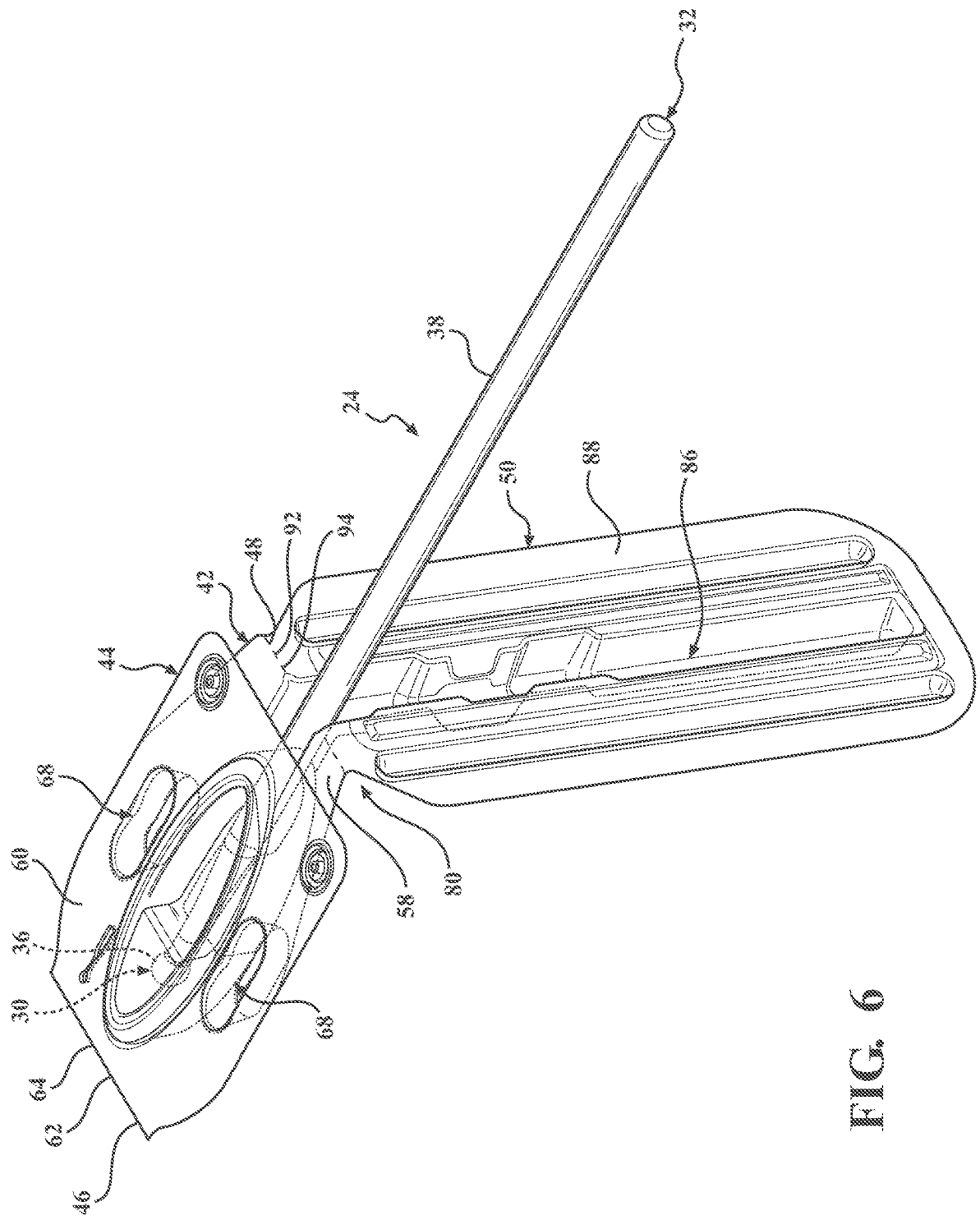
FIG. 6 is a perspective view of the packaging body of FIG. 3 with the elongate tool disposed within the packaging body in an installation configuration.

The proximal section 50 is configured to move between a packaging configuration and an installation configuration. The packaging configuration, as shown in FIGS. 3 and 4, includes the proximal end 32 of the tool 24 disposed within the cavity 86 of the proximal section 50. In the packaging configuration, the primary surfaces 58, 88 of the first distal section 42 and the proximal section 50 may be substantially coplanar. The packaging body 24 may be provided in the packaging configuration prior to installing or mounting the tool 24 on the surgical device 28 in a manner to be described. Referring to FIG. 6, the installation configuration includes pivoting the proximal section 50 relative to the first distal section 42, thereby exposing the proximal end 32 of the tool 24 outside the cavity 86 of the proximal section 50. Moving from the packaging configuration to the installation configuration may comprise pivoting the primary surface 88 of the proximal section 50 relative to the primary surface 58 of the first distal section 42 to expose the proximal end 32 of the tool 24 outside the cavity 86.

The living hinge 92 and the cutouts 80 facilitate the relative pivoting between the first distal section 42 and the proximal section 50 at the proximal boundary 48. The living hinge 92 may be oriented on an axis 96 perpendicular to the tool axis 34 of the tool 24, as shown in FIG. 4, such that the proximal section 50 is pivotally coupled to the first distal section 42 about the axis 96 perpendicular to the tool axis 34 of the tool 24. The axis 96 of the living hinge 92 at the proximal boundary 48 may be oriented parallel to the axis 66 of the living hinge 92 at the distal boundary 46. In other embodiments when the tool 24 is curved, the axis 96 may or may not be perpendicular to the tool axis 34 of the tool 24. For example, the axis 96 may be oriented at any suitable angle relative to the tool axis 34 to accommodate one or more curved portions of the tool 24.

The packaging body 22 of the illustrated embodiments of the present disclosure, with the tool 24 disposed within the cavities 54, 56 extending along a midline of the width, results in a generally symmetric construction of the packaging body 22. It is to be understood that the packaging body 22 need not be symmetric in construction. For example, the illustrated embodiments show the living hinges 62, 92, and the perforations 64, 94 extending across an entirety of a width of the packaging body 22 (e.g., between the cutouts 74, 80). In certain embodiments, the living hinges 62, 92, and/or the perforations 64, 94 may extend across the packaging body 22 for only a portion of the width. In one example, the living hinges 62, 92, and/or the perforations 64, 94 may be positioned entirely to one side of the tool axis 34 of the tool 24. In other words, the living hinges 62, 92, and/or the perforations 64, 94 extend from the cutouts 74, 80 to less than halfway across the width of the packaging body 22 (i.e., the midline of the otherwise symmetric packaging body). Additionally or alternatively, one or more tabs (not shown) may be provided and coupled to or integral with one of the first and second distal sections 42, 44, and/or the proximal section 50. The tab is positioned adjacent the perforation(s) 64, 94 and extend outwardly from the packaging body 22. The tab is adapted to be grasped by a user to effectuate a tearing motion at the perforation(s) 64, 94 with the user supporting the packaging body 22 opposite the perforation 64, 94 to be engaged. The tab may be positioned on one or both sides of the packaging body 22. Furthermore, there may be only one perforation 64, 94 provided to localize the tearing force provided by the user.

The cutouts 80 may be disposed at opposing ends of the proximal boundary 48. The cutouts 80 comprise material removed or absent from one or more of the first distal section 42 and the proximal section 50 at the opposing ends of the proximal boundary 48, as shown in FIGS. 3-5. The cutouts 80 may comprise material removed or absent from one or more of the first distal section 42 and the proximal section 50 at a singular one of the opposing ends of the proximal boundary 48. The cutouts 80 of the illustrative embodiment are generally triangular when viewed in plan, but other suitable shapes are contemplated. The cutouts 80 may localize stresses at the opposing ends of the proximal boundary 48 to facilitate relative pivoting of first distal section 42 and the proximal section 50 at the proximal boundary 48. The relative pivoting is typically imparted by the user holding the packaging body 22. In one example, the user may hold the clamshell casing 52 in one hand and grasp the proximal section 50 with the other hand in order to pivot the proximal section 50 relative to the clamshell casing 52.

Figure 7:
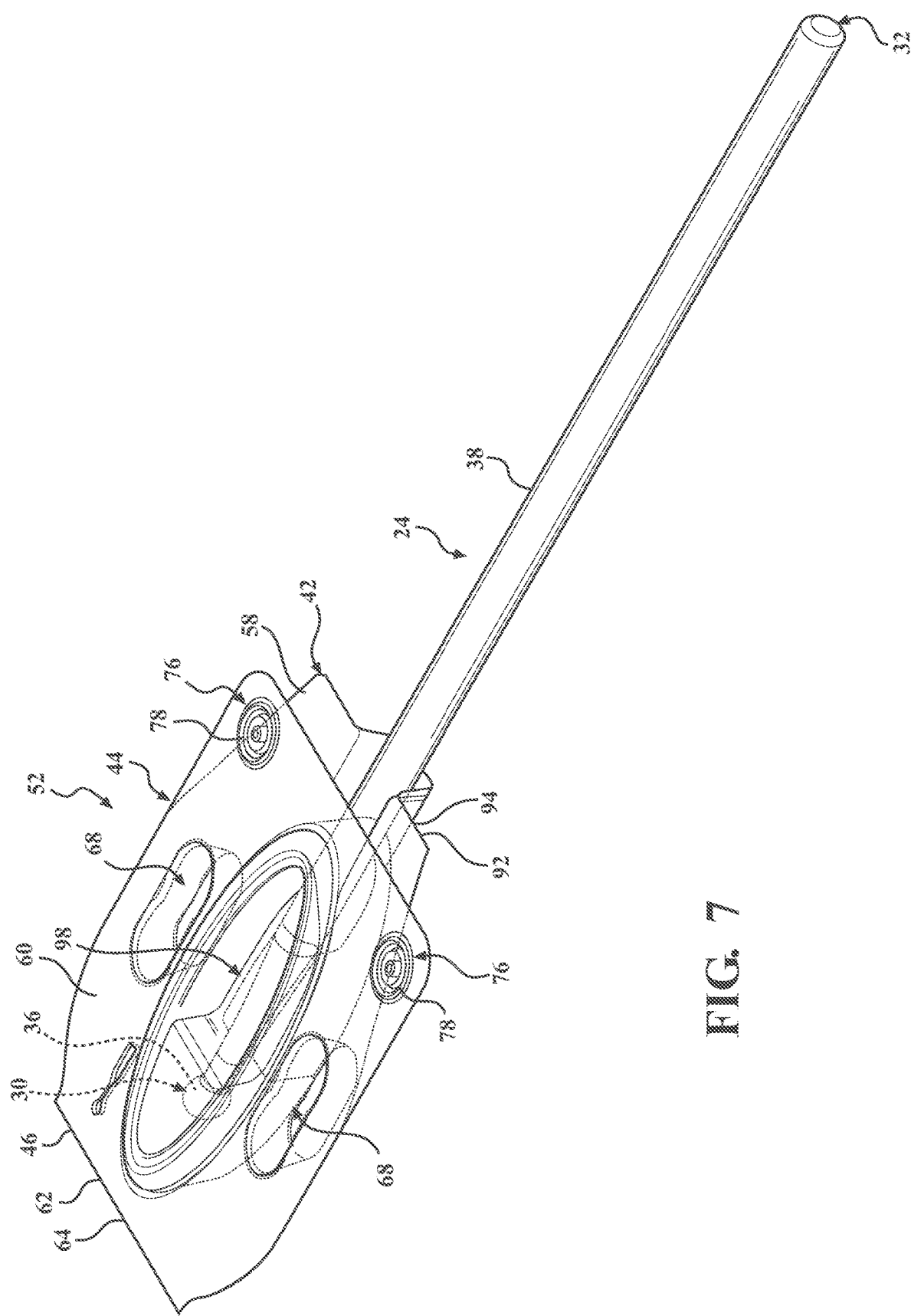
FIG. 7 is a perspective view of the packaging body of FIG. 3 with a proximal section detached from a distal section so as to expose a proximal portion of the elongate tool.

The first distal section 42 may be detachably coupled to the proximal section 50 at the proximal boundary 48. The packaging body 22 comprises the perforation 94 at the proximal boundary 48 configured to facilitate detachment of the first distal section 42 from the proximal section 50, or vice versa. FIG. 7 shows the packaging body 22 subsequent to detachment of the proximal section 50 from the first distal section 42. The proximal section 50 may be detached from the first distal section 42 either prior to or after mounting or installing the tool 24 on the surgical device 28 in a manner to be described. The distal end 30 of the tool 24, including the head 36, may remain safely packaged in the clamshell casing 52 subsequent to detachment of the proximal section 50 from the first distal section 42.

To detach the proximal section 50 from the first distal section 42, the user may provide a force, through bending, pulling, rotating, or combination thereof, sufficient to tear along the perforations 94. The user may support the clamshell casing 52 with the opposing hand, or the tool 24 may be mounted on the surgical device 28 such that no user support may be necessary. Care should be taken to ensure that the force provided to detach the proximal section 50 from the first distal section 42 does not prematurely decouple the couplers 68 of the clamshell casing 52, unless intended by the user.

Figure 8:
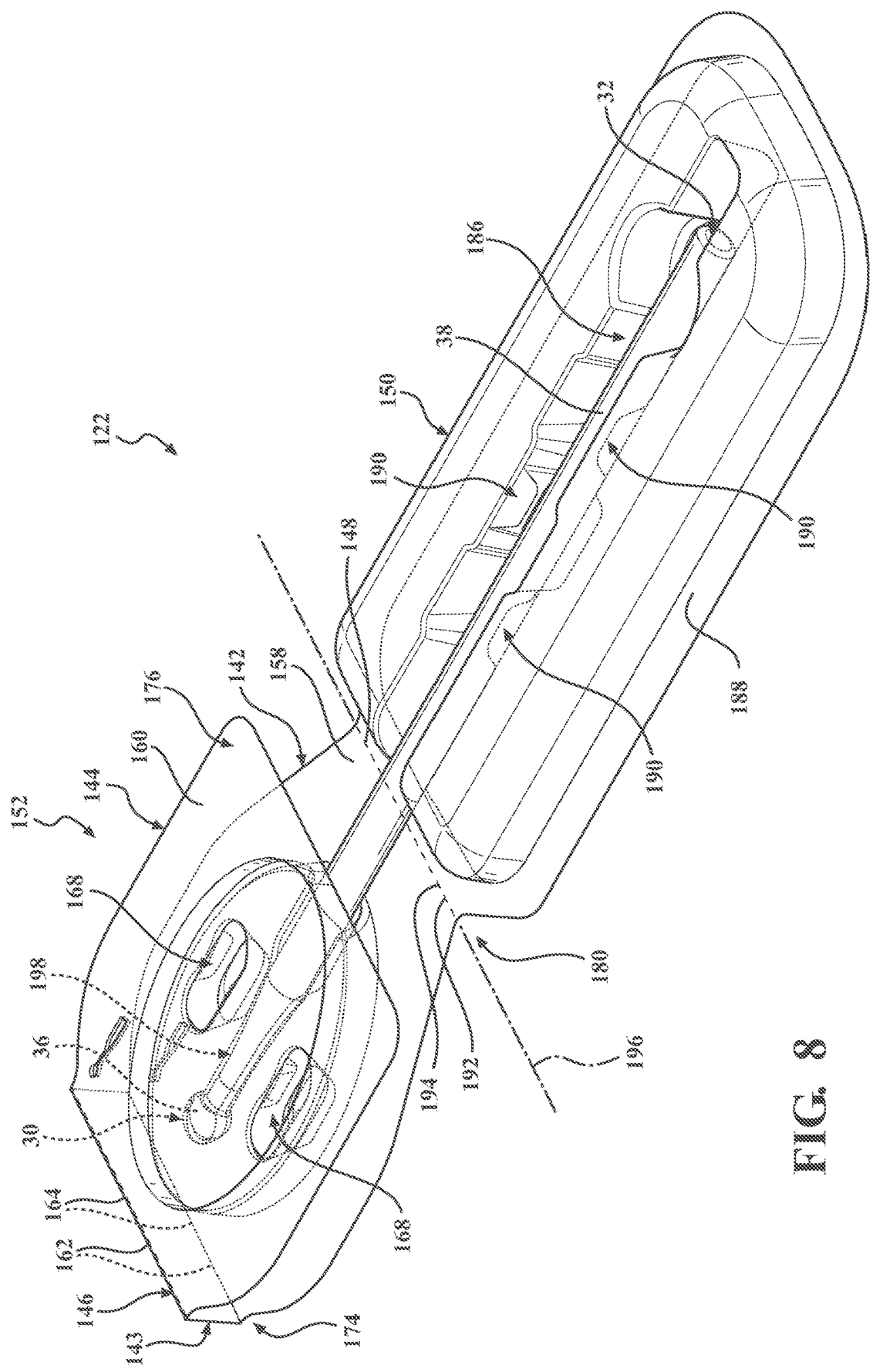
FIG. 8 is a packaging body in accordance with another exemplary embodiment of the present disclosure with the elongate tool disposed within the packaging body in the first configuration.
Figure 9:
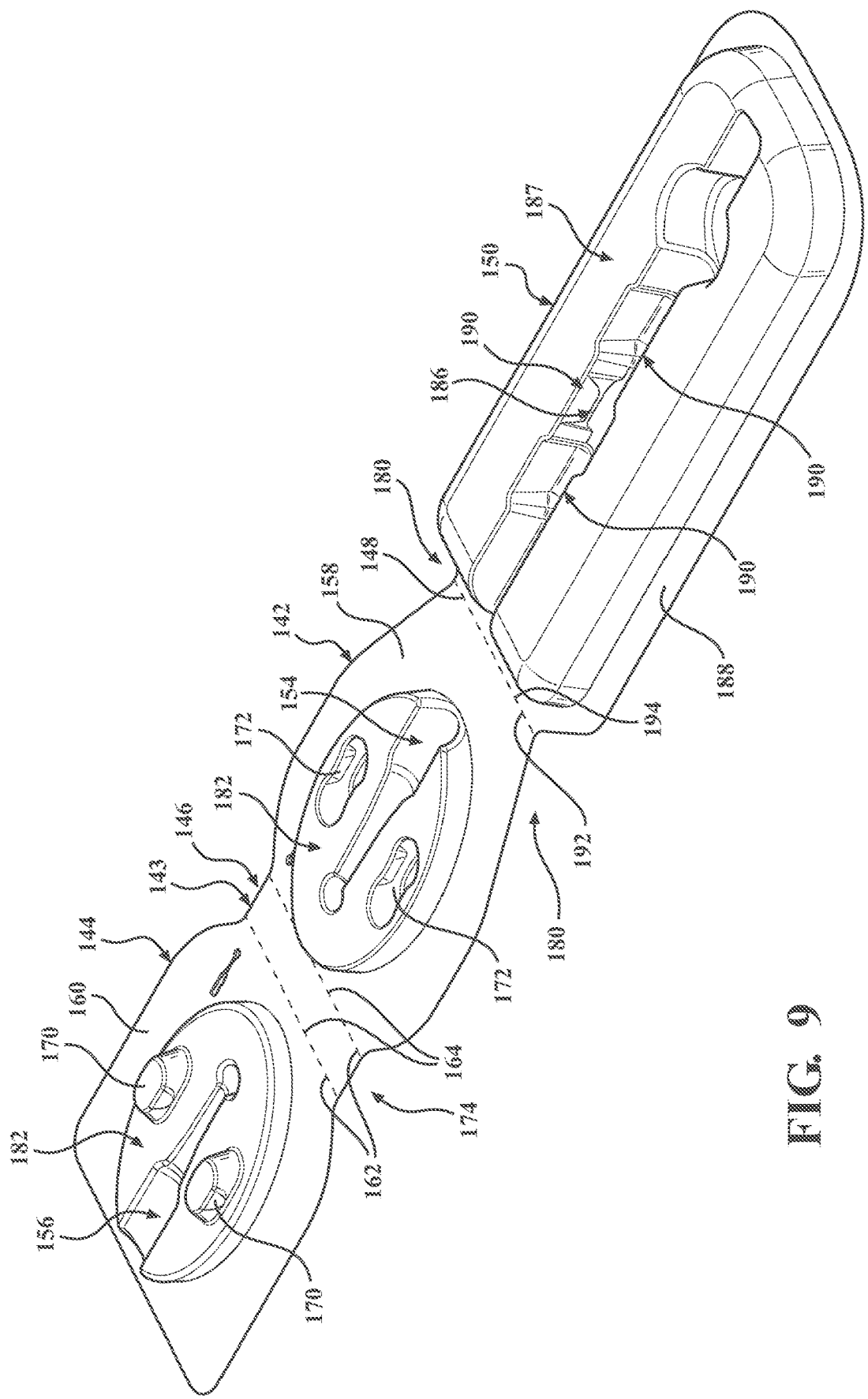
FIG. 9 is a perspective view of the packaging body of FIG. 8 in a second configuration with the elongate tool removed from the packaging body.
Figure 10:
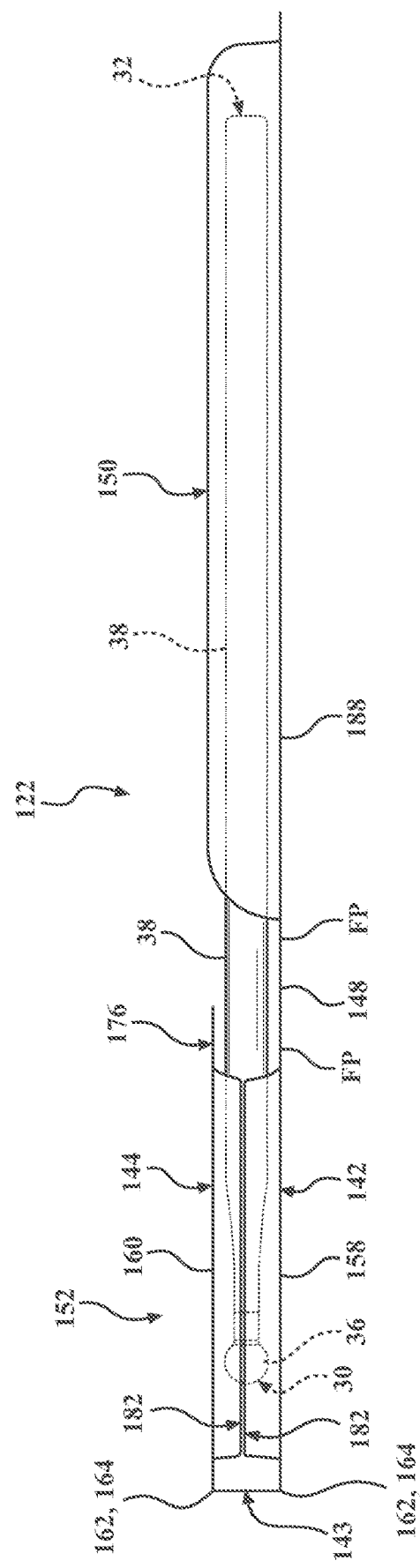
FIG. 10 is a side elevation view of the packaging body of FIG. 8 with the elongate tool disposed within the packaging body in the first configuration.

FIGS. 8-10 show a segmented packaging body 122 in accordance with another exemplary embodiment of the packaging system 20. Like components of the packaging body 22 of the previously described embodiment are identified with a reference numeral increased by one hundred (100). Disclosure for the present embodiment of the packaging body 122 abbreviated from the previously described embodiment is not to be construed as limiting unless specifically indicated.

The packaging body 122 is configured to removably receive the elongate tool 24 configured to be mounted on the surgical device 28. Secondary packaging 26, such as the sealed pouch, the blister pack, or the like, may be provided and configured to receive the packaging body 122. The packaging body 122 comprises the first distal section 142 and the second distal section 144. The first distal section 142 comprises the distal boundary 146 and the proximal boundary 148. The second distal section 144 is coupled to the first distal section 142 at the distal boundary 146. The packaging body 122 further comprises the proximal section 150 coupled to the first distal section 142 at the proximal boundary 148.

The packaging body 122 may further comprise a transition section 143 coupled to and positioned intermediate the first and second distal sections 142, 144. Based on the structure of the clamshell casing 152 of the present embodiment to be described, the transition section 143 provides spacing between the primary surfaces 158, 160 of the first and second distal sections 142, 144 such that, in the first configuration, the first and second distal sections 142, 144 are in the desired abutting relationship. The transition section 143 may define the distal boundary 146.

The transition section 143 may comprise two or more living hinges 162 separated by a surface. FIG. 8 shows the transition section 143 with two living hinges 162 such that, in the first configuration, the transition section 143 and first and second distal sections 142, 144 assume a substantially U-shaped configuration. The living hinges 162 may be described as a thin, flexible connection or web pivotally coupling each of the first and second distal sections 142, 144 with the transition section 143. Perforations 164 may be associated with each of the living hinges 162 such that the first distal section 142, the transition section 143, and/or the second distal section 144 are selectively detachable from one another.

The first and second distal sections 142, 144 are configured to receive the distal end 30 of the tool 24. FIG. 8 shows the first and second distal sections 142, 144 receiving the distal end 130 and a portion of the shaft 38 of the tool 24. The first and second distal sections 142, 144 may be pivotally coupled to provide the clamshell casing 152 to the distal end 30 of the tool 24.

The clamshell casing 52 may be provided by the cavity 154, 156 disposed in each of the first and second distal sections 142, 144. With reference to FIG. 9, the first distal section 142 comprises the primary surface 158 extending between the distal boundary 146 and the proximal boundary 148. The second distal section 144 comprises the primary surface 160. The primary surfaces 158, 160 may be considered as substantially flat portions of first and second distal sections 142, 144. Each of the first and second distal sections 142, 144 may comprise the boss 182 configured to support the tool 24 proximate the distal end 30. In the packaging body 122 of the present embodiment, the bosses 122 extend from the primary surfaces 158, 160 of the first and second distal sections 142, 144. The boss 182 comprise the cavities 154, 156 configured to receive the shaft 38 of the tool 24 proximal the head 36. The cavity 154, 156 may be substantially contoured to a distal region of the tool 24 such that, when the couplers 168 are coupled in the first configuration, the shaft 38 of the tool 24 proximal the head 36 is securely encased within the clamshell casing 152.

The cavities 154, 156 of each of the first and second distal sections 142, 144 may be in substantial alignment so as to receive the distal end 30 of the tool 24 in a first configuration. The clamshell casing 152 may be provided by articulating one of the first and second distal sections 142, 144 relative to the other between the first configuration shown in FIG. 8, and the second configuration shown in FIG. 9. The second distal section 144 may be pivotally coupled to the first distal section 142 at the distal boundary 146 comprising the living hinges 162 oriented perpendicular to the tool axis 34 of the tool 24. In the present embodiment, the boss 182 of each of the first and second distal sections 142, 144 are provided in a direct abutting relationship in the first configuration. With reference to FIG. 10, because the boss 182 of each of the first and second distal sections 142, 144 extend from the primary surfaces 158, 160 (with no cavity of the previously described embodiment), spacing is required between the primary surfaces 158, 160 to directly abut the bosses 182 in a flat-on-flat manner. The transition region 143 is suitably sized to provide the spacing required to achieve the direct abutting relationship shown in FIGS. 8 and 10. The primary surfaces 158, 160 of the first and second distal sections 142, 144 may be substantially parallel in the first configuration. The first and second distal sections 142, 144 are positioned in a non-abutting relationship in the second configuration as shown in FIG. 9 (with the tool 24 removed).

The packaging body 122 further comprises the couplers 168 removably coupling the first and second distal sections 142, 144. The couplers 168 are configured to maintain the first and second distal sections 142, 144 in the first configuration absent the input from the user. In certain embodiments, the couplers 168 comprise the protrusion 170 removably coupled to the recess 172 by interference fit in the first configuration. The recess 172 may be provided within the boss 182 of one of the first and second distal sections 142, 144, and the protrusion 170 provided within the boss 182 on the other one of the first and second distal sections 142, 144. In the exemplary embodiment shown in FIGS. 8 and 9, two recesses 172 and two protrusions 170 are provided. The protrusions 170 and recesses 172 are positioned on opposing sides of the cavities 154, 156 of the boss 182 of each of the first and second distal sections 142, 144. The interference fit between the protrusion 170 and the recess 172 maintains the clamshell casing 152 such that the first and second distal sections 142, 144 encase the distal end 30 of the tool 24.

Moving the packaging body 122 from the first configuration to the second configuration comprises pivoting one of the first and second distal sections 142, 144 about the distal boundary 146 comprising the living hinges 162 oriented transverse to the tool axis 34. The desired movement may be further facilitated by the cutouts 174 comprising material removed or absent from one or more of the first and second distal sections 142, 144 at the opposing ends of the living hinges 162, as shown in FIGS. 8 and 9. In the second configuration, the cutouts 174 may be trapezoidal when viewed in plan, but other suitable shapes are contemplated. The cutouts 174 may localize stresses in a suitable manner to facilitate relative pivoting of first and second distal sections 142, 144 relative to the transition section 143 and one another.

The relative pivoting is typically imparted by the user holding the packaging body 122. In one example, the user may hold the proximal section 150 and/or the first distal section 142 in one hand and grasp the second distal section 144 with the other hand in order to overcome the interference fit of the couplers 168. The user may use fingers to pinch or grasp the second distal section 144 while holding of the first distal section 142. The spacing between the primary surfaces 158, 160 may provide clearance for the user to pinch or grasp the primary surface 160 of the second distal section 144. The packaging body 22 may further comprise the finger grip 176 comprising a portion of the primary surface 160 of the second distal section 144 extending outwardly from the first distal section 142. The finger grip 176 may be positioned adjacent and/or proximate to the cutouts 180 associated with the proximal boundary 148.

The packaging body 122 comprises the proximal section 150 coupled to the first distal section 142 at the proximal boundary 148. The proximal section 150 may further comprise the primary surface 188 coupled to the primary surface 158 of the first distal section 142 at the proximal boundary 148. The proximal section 150 is configured to receive a proximal portion of the shaft 38 of the tool 24 comprising the proximal end 32.

The proximal section 150 comprises the cavity 186 configured to receive the proximal portion of the tool 24. The cavity 186 may be provided within a proximal shelf 187. The proximal shelf 187 extends from the primary surface 188 of the proximal section 150 and defines the cavity 186. The proximal shelf 187 defining the cavity 186 is suitably sized such that the cavity 186 of the proximal section 150 and the cavity 154 of the first distal section 142 are aligned (e.g., substantially collinear). FIG. 9 shows the cavity 186 is elongate and suitably sized to receive the tool 24. The tool 24 may be secured within the cavity 186 with the one or more shaft couplers 190 which comprise, for example, the protrusions with the counterposing recesses to provide the interference fit to the shaft 38 of the tool 24. The interference fit may be provided by a small amount of elastic deformation of the shaft coupler 190 that occurs as the tool 24 is urged within the cavity 186 of the proximal section 150.

The cavity 154 of the first distal section 142 and the cavity 186 of the proximal section 150 may be separated by flat portions of the first distal section 142 and the proximal section 150. Referring to FIGS. 8-10, the flat portion of the first distal section 142 may be defined as the primary surface 158 intermediate the boss 182 and the proximal boundary 148 (see FP of FIG. 10). The flat portion of the proximal section 152 may be defined as the primary surface 188 intermediate the proximal shelf 187 and the proximal boundary 148. The flat portions provide for, among other things, the proximal boundary 148 being linear. Consequently, the living hinge 192 and the perforations 194 at the proximal boundary 148 are linear. The living hinge 192 being linear may facilitate easier relative pivoting between the first distal section 142 and the proximal section 150 with greater magnitudes of articulation. The perforation 194 being linear may facilitate easier detachment of the proximal section 150 from the first distal section 142 relative to more complex geometries.

The proximal section 150 is configured to move between the packaging configuration and the installation configuration. The packaging configuration, as shown in FIG. 8, includes the proximal end 32 of the tool 24 disposed within the cavity 186 of the proximal section 150. In the packaging configuration, the primary surfaces 158, 188 of the first distal section 142 and the proximal section 150 may be substantially coplanar. The flat portions may result in a portion of the shaft 38 of the tool 24 being exposed in the packaging configuration, as shown in FIG. 10. FIG. 8 also shows the first and second distal sections 142, 144 in the first configuration; e.g., the boss 182 of the first and second distal sections 142, 144 are positioned in an abutting relationship. In the first configuration, the primary surfaces 158, 160 of the first and second distal sections 142, 144 may be substantially parallel.

The installation configuration includes pivoting the proximal section 150 relative to the first distal section 142, thereby exposing the proximal end 32 of the tool 24 outside the cavity 186 of the proximal section 150. The proximal section 150 may be configured to be moved from the packaging configuration to the installation configuration while the first and second distal sections 142, 144 are in the first configuration. The living hinge 192 and the cutouts 180 facilitate the relative pivoting between the first distal section 142 and the proximal section 150 at the proximal boundary 148. The living hinge 192 may be oriented on the axis 196 (see FIG. 8) perpendicular to the tool axis 34 of the tool 24, and parallel to the living hinges 162 at the distal boundary 146. The cutouts 180 may comprise material removed or absent from one or more of the first distal section 142 and the proximal section 150 at the opposing ends of the proximal boundary 148. The tool 24 may be mounted on the surgical device 28 while the packaging body 122 is in the installation configuration as to be described.

The first distal section 142 may be detachably coupled to the proximal section 150 at the proximal boundary 148. The packaging body 122 comprises the perforations 194 at the proximal boundary 148 configured to facilitate detachment of the first distal section 142 from the proximal section 150, or vice versa. To detach the proximal section 150 from the first distal section 142, the user may provide a force, through bending, pulling, rotating, or combination thereof, sufficient to tear along the perforations 194. The proximal section 150 may be detached from the first distal section 142 after mounting or installing the tool 24 on the surgical device 28. The distal end 30 of the tool 24, including the head 36, may remain safely packaged in the clamshell casing 152 subsequent to detachment of the proximal section 150 from the first distal section 142.

Exemplary methods of mounting the elongate tool 24 on the surgical device 28 are also disclosed. FIG. 11 shows the robot R having an end effector EE, which comprises a non-limiting example of the surgical device 28. It is to be understood the methods described herein may be applicable to any number and type of tools and surgical devices, and the surgical device 28 need not comprise the robot R and/or the end effector EE. In certain embodiments, the packaging system 20 and exemplary methods may be utilized to mount the tool 24 to a handheld powered surgical device such as a bone drill, oscillating saw, and the like. In other embodiments, the tool 24 may be mounted to a handheld and non-powered surgical device such as a scalpel, an endoscope, and the like. The tool 24 need not comprise a cutting accessory with sharp features. Further, the exemplary methods of mounting the tool 24 may not require that the tool 24 need be sterilized. FIGS. 13-22 show a representative example of the end effector EE to describe the methods of mounting the tool 24 on the surgical device 28, and the representative example should not be construed as limiting.

The tool 24 comprises the distal end 30 opposite the proximal end 32. The method may include providing the distal end 30 of the tool 24 within a distal cavity defined between the first distal section 42, 142 and the second distal section 44, 144. In certain embodiments, the distal cavity may be defined as the combination of the cavity 54, 154 of the first distal section 42, 142 and the cavity 56, 156 of the second distal section 44, 144. The distal cavity is referenced in FIGS. 3 and 7 as reference numeral 98 and in FIG. 8 as reference numeral 198.

Figure 12:
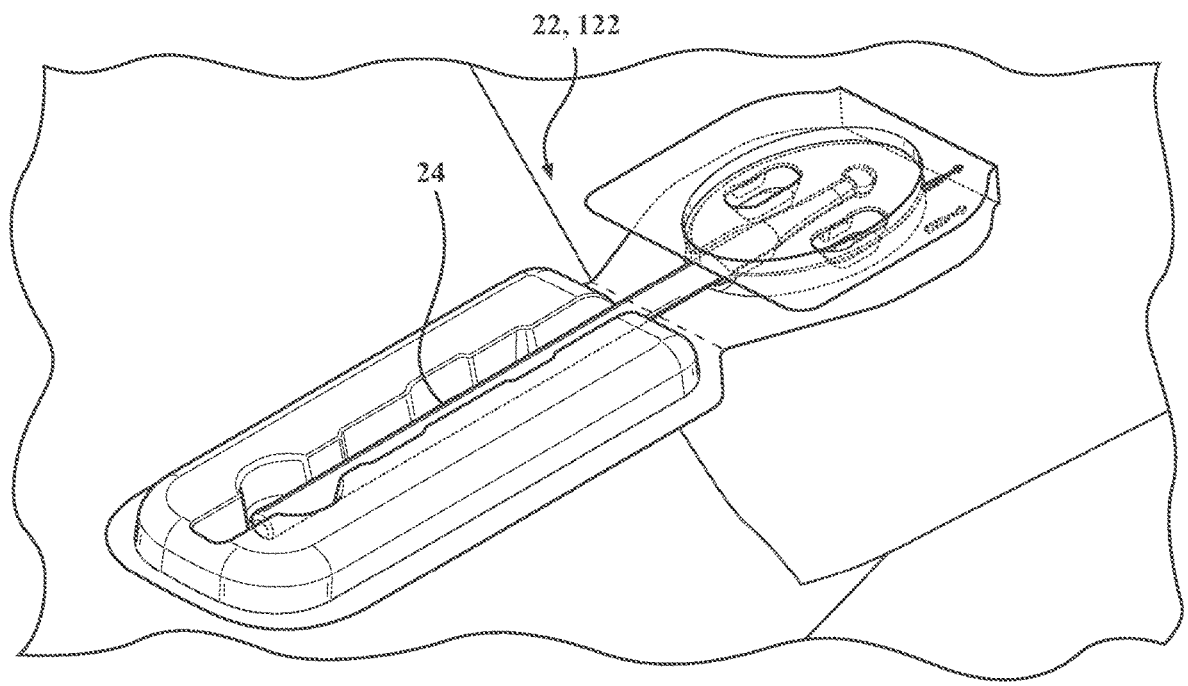
FIG. 12 shows a step of an exemplary method of mounting the elongate tool on the surgical device.

Referring to FIG. 12, the tool 24 is disposed within the segmented packaging body 22, 122. FIGS. 12-22 show the packaging body 122 of the embodiment illustrated in FIGS. 8-10. It is to be understood the exemplary methods may be similarly performed with the embodiment illustrated in FIGS. 1-7. The packaging body 22, 122 including the tool 24 is initially positioned away from the end effector EE. The packaging body 22, 122 may be disposed with secondary packaging 26 such as the sealed pouch or the blister pack. Exemplary methods may comprise removing the packaging body 22, 122 from the secondary packaging 26.

With concurrent reference to FIGS. 3 and 8, FIG. 12 shows the packaging body 22, 122 in the first configuration and the packaging configuration. The first configuration comprises the first distal section 42, 142 and the second distal section 44, 144 positioned in the abutting relationship such that the distal end 30 of the tool 24 is encased in the clamshell casing 52, 152. In the first configuration, the distal end 30 of the tool 24 is disposed within the cavity 54, 154 of the first distal section 42, 142 and the proximal end 32 of the tool 24 is disposed within the cavity 86, 186 of the proximal section 50, 150. The primary surface 58, 158 of the first distal section 42, 142 and the primary surface 60, 160 of the second distal section 44, 144 may be substantially parallel in the first configuration. The packaging configuration comprises the proximal end 32 of the tool 24 disposed within the cavity 86, 186 of the proximal section 50, 150. The primary surface 58, 158 of the first distal section 42, 142 and the primary surface 88, 188 of the proximal section 50, 150 may be substantially coplanar in the packaging configuration. The packaging configuration may further be associated with the packaging body 22, 122, being in the first configuration as reflected in FIGS. 3, 8 and 12.

Figure 13:
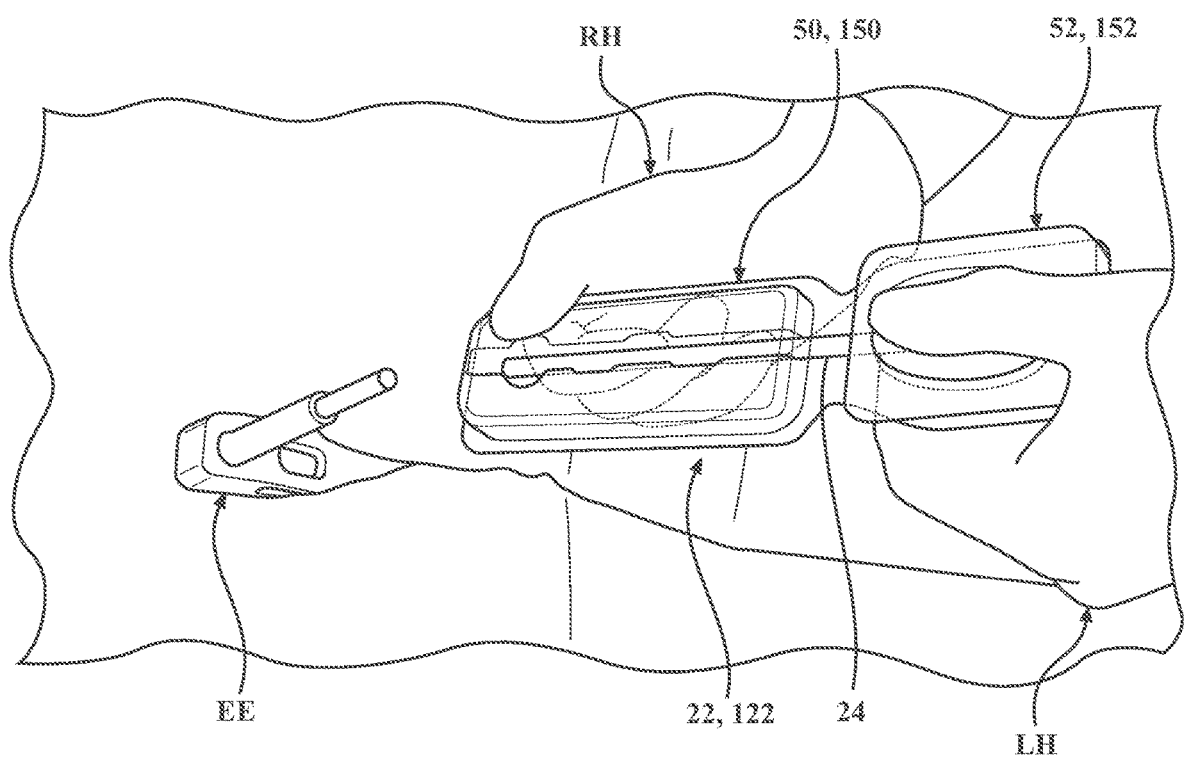
FIG. 13 shows another step of the exemplary method of mounting the elongate tool on the surgical device.
Figure 14:
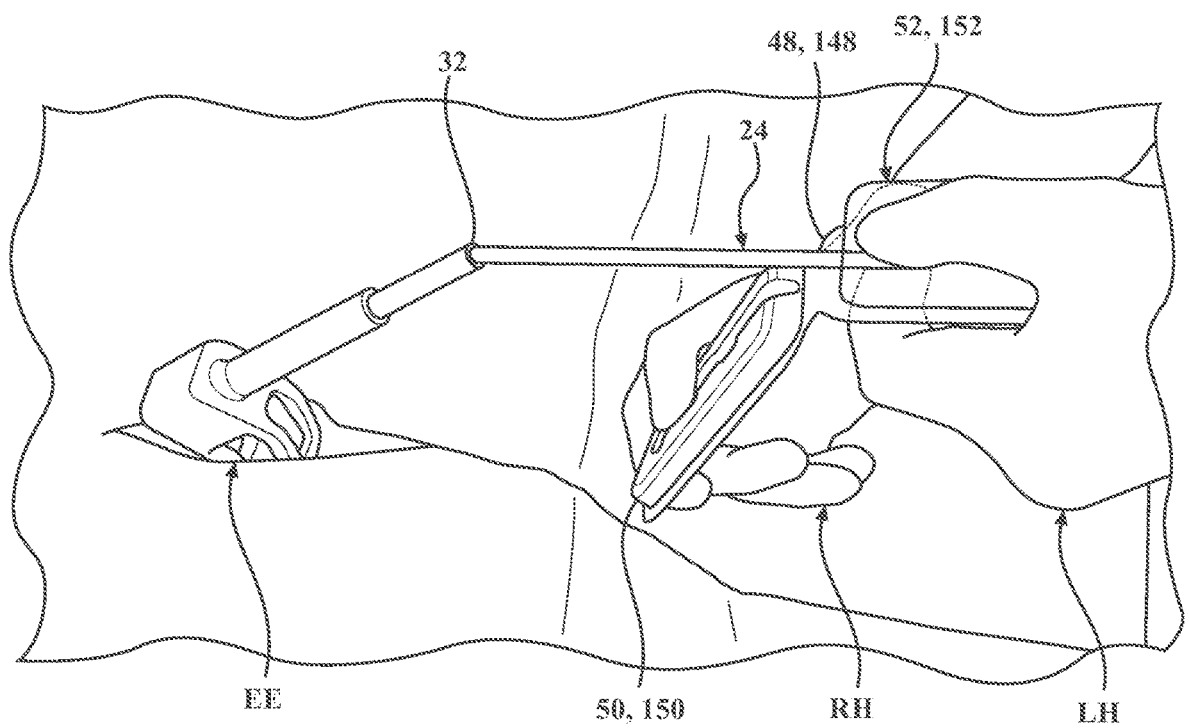
FIG. 14 shows another step of the exemplary method of mounting the elongate tool on the surgical device.

The user grasps the packaging body 22, 122 with, for example, the right hand RH and the left hand LH as shown in FIG. 13. Since the proximal end 32 of the tool 24 is to be mounted on the end effector EE, the user may grasp the packaging body 22, 122 by the clamshell casing 52, 152 with the proximal section 50, 150 of the packaging body 22, 122 oriented towards the end effector EE. FIG. 13 shows the user grasping the clamshell casing 52, 152 with the left hand LH and the proximal section 50, 150 with the right hand RH. While holding the packaging body 22, 122, the method comprises articulating the proximal section 50, 150 about the proximal boundary 48, 148 relative to the first distal section 42, 142 to remove the proximal end 32 of the tool 24 from the cavity 86, 186 of the proximal section 50, 150. FIG. 14 shows the user articulating the proximal section 50, 150 with the right hand RH while supporting the clamshell casing 52, 152 with the left hand LH. The user may pinch between a thumb and index finger the clamshell casing 52, 152 so as to maintain the clamshell casing 52, 152 in the first configuration and avoid inadvertent decoupling of the first distal section 42, 142 and the second distal section 44, 144. The relative articulation exposes the proximal end 32 of the tool 24.

The relative articulation may be imparted by the left hand LH of the user. The proximal section 50, 150 may pivot about the living hinge 92, 192 at the proximal boundary 48, 148, and the cutouts 80, 180 may facilitate the pivoting. The pivoting of the proximal section 50, 150 relative to the first distal section 42, 142 to expose the proximal end 32 of the tool 24 comprises moving the packaging body 22, 122 from the packaging configuration to the installation configuration.

Figure 15:
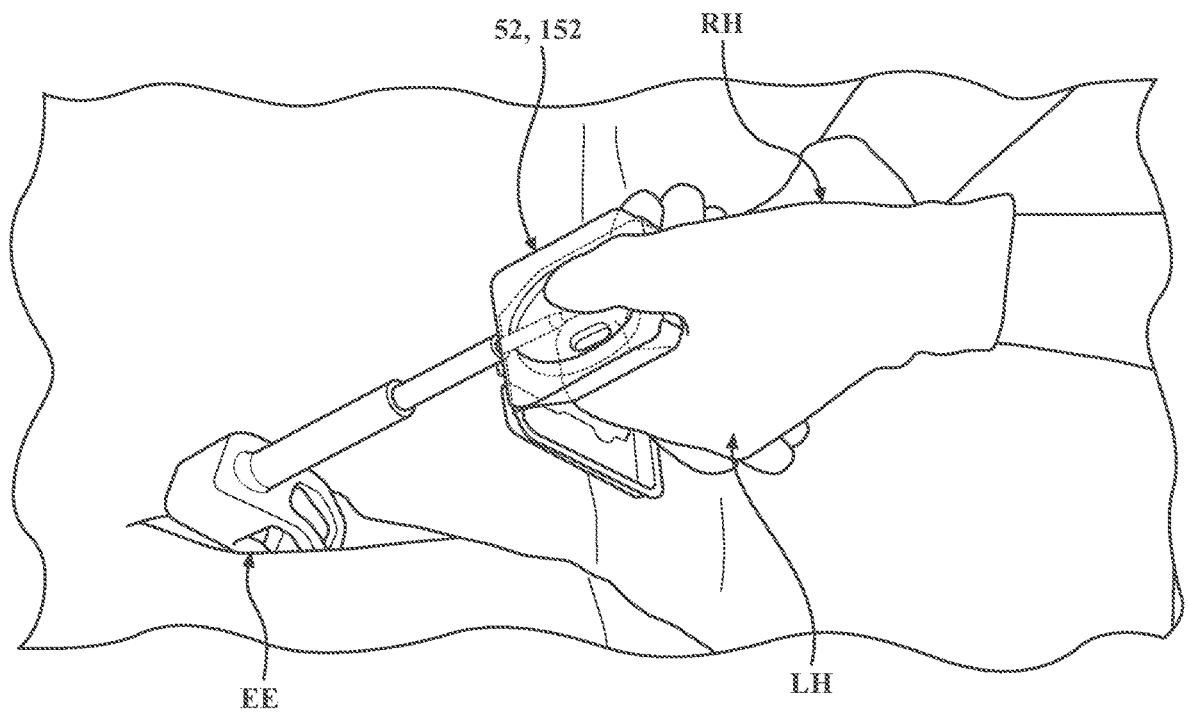
FIG. 15 shows another step of the exemplary method of mounting the elongate tool on the surgical device.

Referring to FIGS. 14 and 15, the proximal end 32 of the tool 24 is mounted on the surgical device 28 while the distal end 30 of the tool 24 remains disposed within the distal cavity 98, 198 in the clamshell casing 52, 152. In other words, the tool 24 is installed while the packaging body 22, 122 is in the first configuration and the installation configuration. FIG. 14 shows the step of mounting comprises inserting the proximal end 32 of the tool 24 within the end effector EE. The packaging body 22, 122 is configured to be grasped by the user when the tool 24 is mounted on the surgical device 28 while the packaging body 22, 122 is in the installation configuration as to avoid user contact with the tool 24. FIG. 15 shows the user slidably moving the tool 24 into a desired engagement with the end effector EE while supporting the packaging body 22, 122. The user is supporting the clamshell casing 52, 152 with the left hand LH and the proximal section 50, 150 with the right hand RH as the shaft 38 of the tool 24 is slidably received with the end effector EE.

After mounting the proximal end 32 of the tool 24 on the surgical device 28, the method may further comprise the step of detaching the proximal section 50, 150 from the first distal section 42, 142 at the proximal boundary 48, 148. The proximal boundary 48, 148 comprises the perforations 94, 194 to facilitate detaching the proximal section 50, 150 from the first distal section 42, 142 at the perforations 94, 194. Subsequent to detachment of the proximal section 50, 150, the remainder of the packaging body 22, 122 assumes the configuration shown in FIG. 18.

Figure 16:
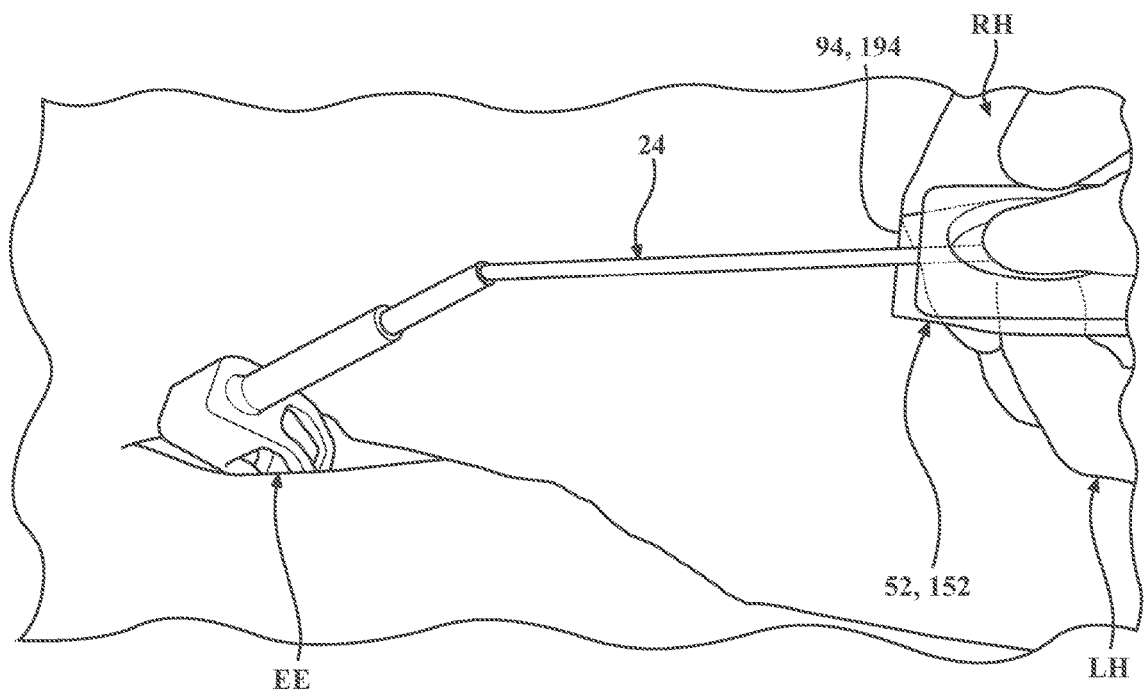
FIG. 16 shows another step of the exemplary method of mounting the elongate tool on the surgical device.
Figure 17:
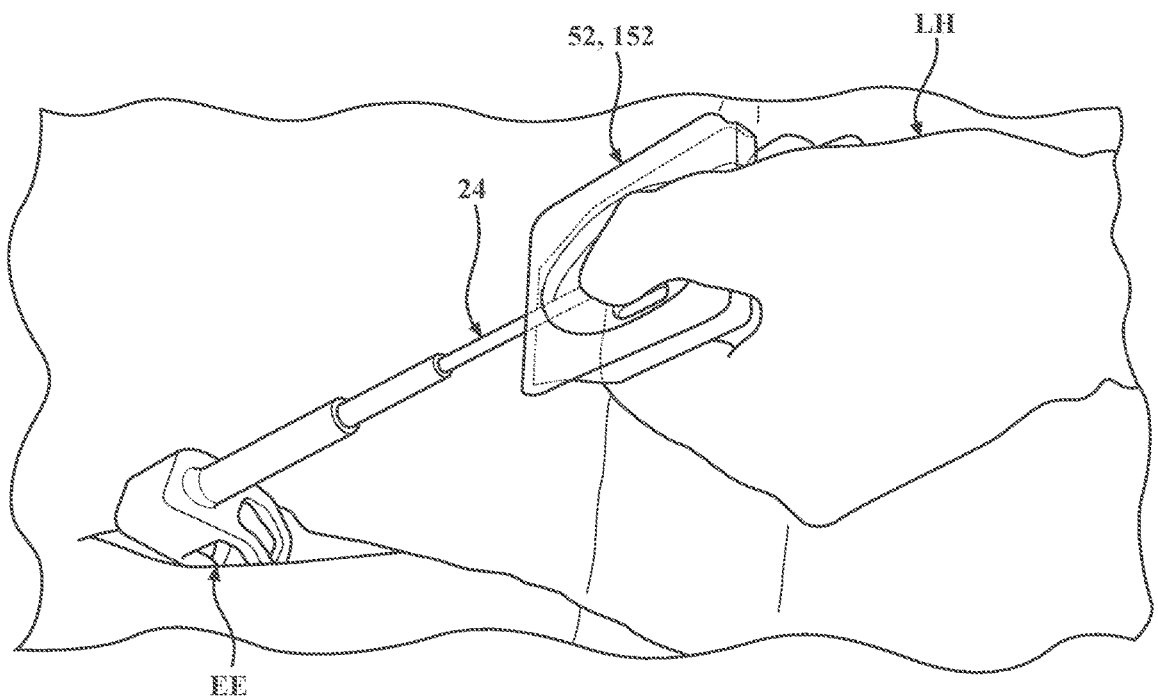
FIG. 17 shows another step of the exemplary method of mounting the elongate tool on the surgical device.
Figure 18:
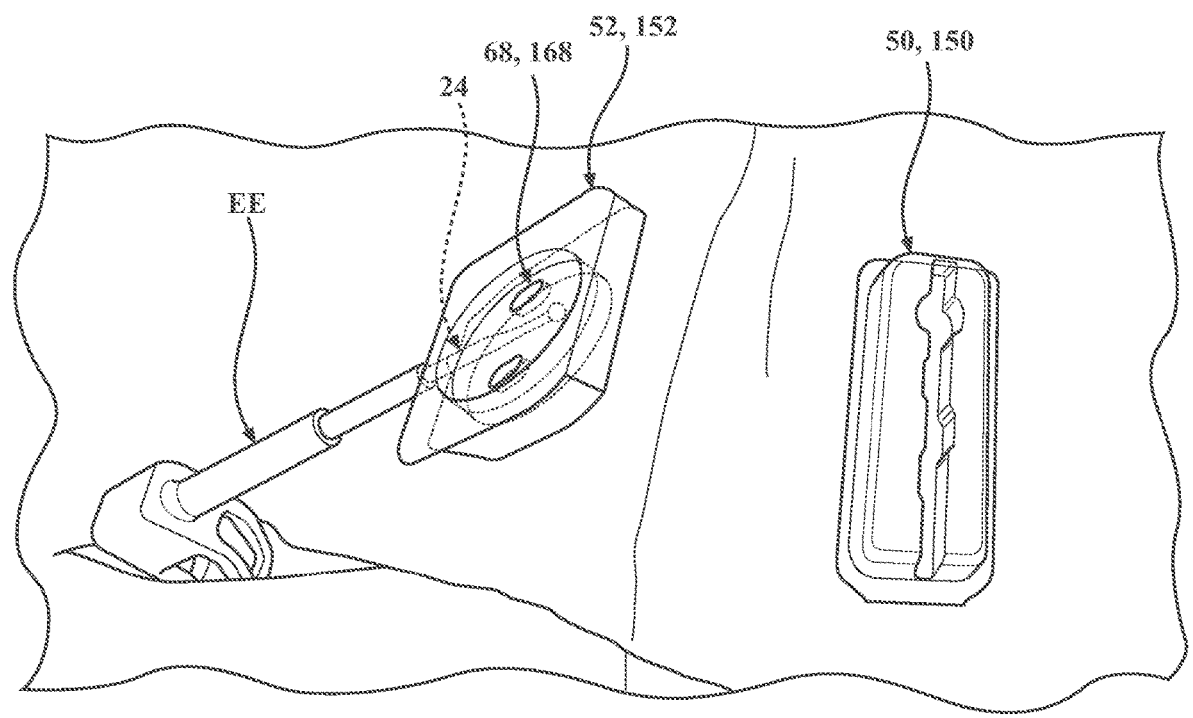
FIG. 18 shows another step of the exemplary method of mounting the elongate tool on the surgical device.

In another exemplary method, the proximal section 50, 150 may be detached from the first distal section 42, 142 prior to mounting or installing the tool 24 on the surgical device 28. Referring to FIGS. 16 and 17, the clamshell casing 52, 152 is shown without the proximal section 50, 150. The user detaches the proximal section 50, 150 from the first distal section 42, 142 at the perforations 94, 194. With one or both of the right hand RH and the left hand LH, the user mounts the proximal end 32 of the tool 24 on the surgical device 28. FIG. 16 shows the user supporting the clamshell casing 52, 152 with both the right hand RH and the left LH, and FIG. 17 shows the user supporting the clamshell casing 52, 152 with the left hand LH. The user may remove one of the hands RH, LH after a portion of the shaft 38 of the tool 24 is confidently within the end effector EE such that suitable engagement is ensured. The right hand RH of the user is now free to perform any other number of tasks related or unrelated to mounting the tool 24 on the surgical device 28. The packaging body 22, 122 assumes the configuration shown in FIG. 18.

Figure 19:
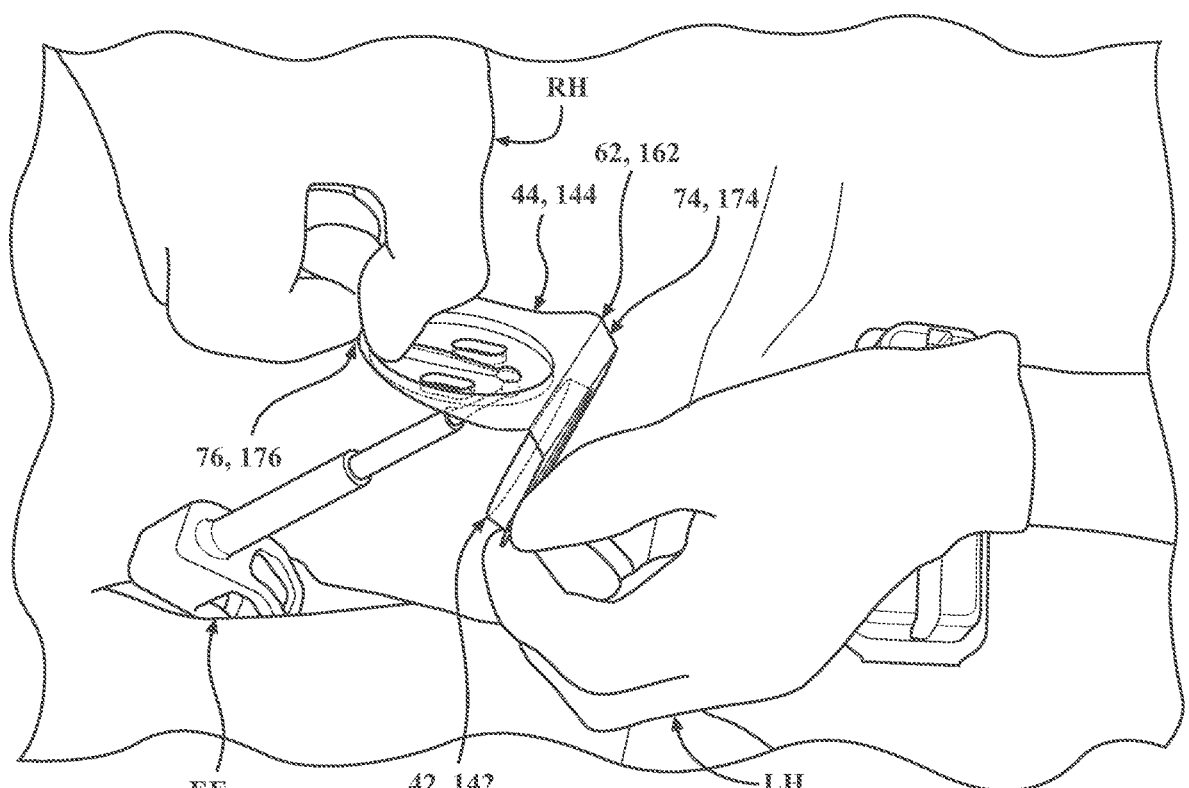
FIG. 19 shows another step of the exemplary method of mounting the elongate tool on the surgical device.
Figure 20:
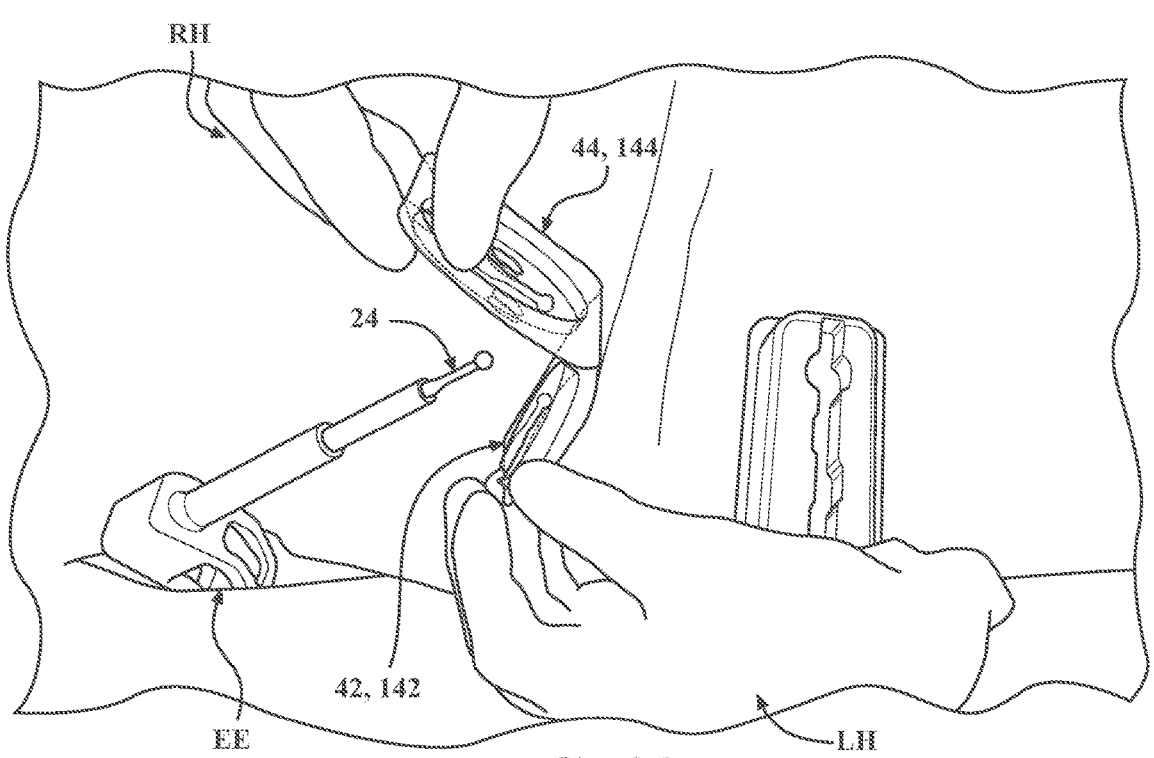
FIG. 20 shows another step of the exemplary method of mounting the elongate tool on the surgical device.
Figure 21:
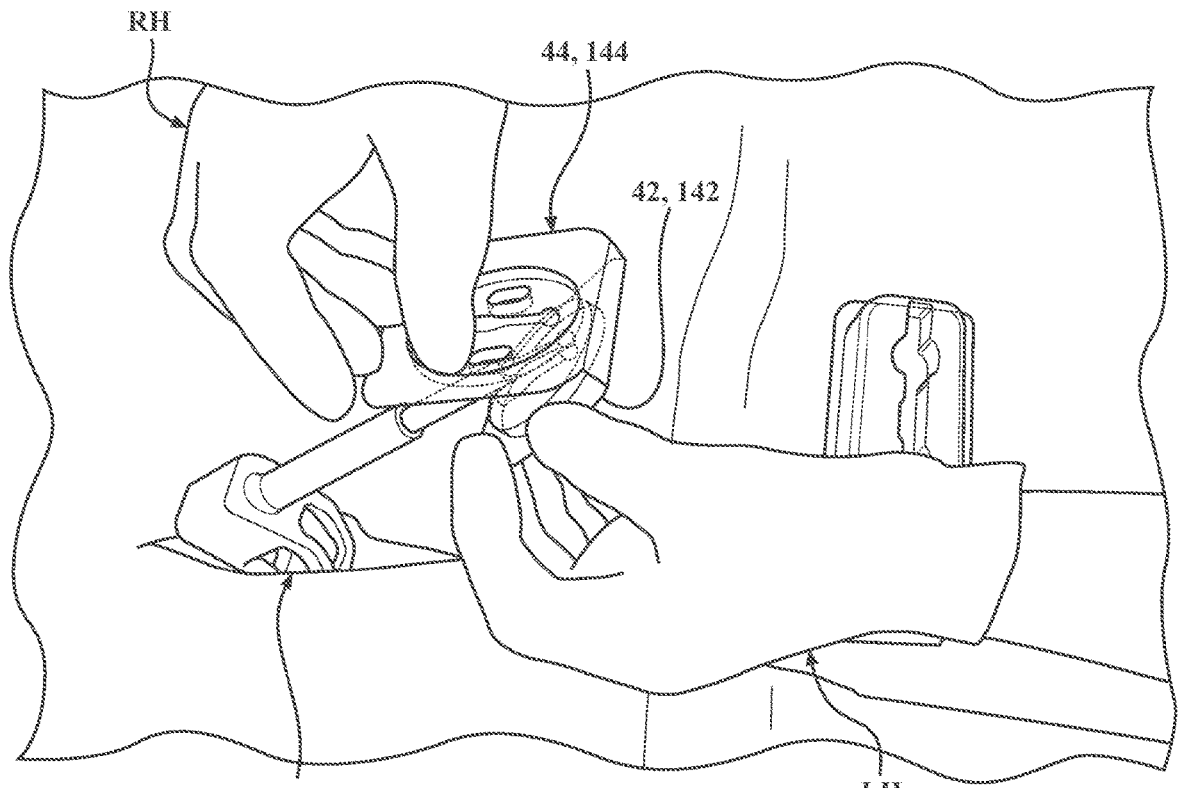
FIG. 21 shows a step of coupling a clamshell casing of the packaging body to the elongate tool.

In certain embodiments, the method further includes articulating one of the first distal section 42, 142 and the second distal section 44, 144 about the distal boundary 46, 146 relative to the other to expose at least a portion of the distal end 30 of the tool 24. FIGS. 19 and 20 show the user moving the packaging body 22, 122 from the first configuration to the second configuration. In the second configuration, the first distal section 42, 142 and the second distal section 44, 144 are in a non-abutting relationship. Stated simply, the user is opening the clamshell casing 52, 152 encasing the distal end 30 of the tool 24. In the illustrative embodiment of FIG. 16, the proximal section 50, 150 is no longer coupled to the first distal section 42, 142 before the packaging body 22, 122 is moved from the first configuration to the second configuration.

To articulate one of the first distal section 42, 142 and the second distal section 44, 144 about the distal boundary 46, 146, the user may grasp the first distal section 42, 142 and pinch or grasp a portion of the second distal section 44, 144, such as with the finger grips 76, 176. The step of articulating may further include decoupling the couplers 68, 168. The force applied by the user to the second distal section 44, 144 overcomes the interference fit provided by the couplers 68, 168 (see FIG. 18). The living hinge 62, 162 and/or the cutouts 74, 174 facilitate the relative pivoting between the first distal section 42, 142 and the second distal section 44, 144 at the distal boundary 46, 146. The user removes the other one of the first distal section 42, 142 and the second distal section 44, 144 from the distal end 30 of the tool 24. The user removes the packaging body 22, 122 from the head 36 of the tool 24 with sufficient clearance to avoid contamination. The head 36 of the tool 24 is now exposed and ready for use during a surgical procedure. It is to be appreciated that the user has not touched the tool 24 in any significant manner, and the head 36 of the tool 24 was shielded from contamination.

In another exemplary method, the user may wish to delay between the step of mounting the tool 24 on the surgical device 28 and/or removing the packaging body 22, 122 to expose the distal end 30 of the tool 24. For example, an operating room technician may mount the tool 24 on the end effector EE well in advance of the surgical procedure. For any desired amount of time, the packaging body 22, 122 may remain in the configuration shown in FIG. 18. The remainder of the packaging body 22, 122 is in the first configuration such that the first distal section 42, 142 and the second distal section 44, 144 are in the abutting relationship. The head 36 of the tool 24 remains secured and protected within the clamshell casing 52, 152 after the tool 24 is mounted on the surgical device 28. Should inadvertent contact occur with the tool 24, the risk of contamination and/or injury to the user and/or surgical device 28 is greatly reduced.

Once desired, the clamshell casing 52, 152 may be removed from the tool 24 to expose the distal end 30 of the tool 24. After the step of detaching the proximal section 50, 150 from the first distal section 42, 142, one of the first distal section 42, 142 and the second distal section 44, 144 is articulated relative to one another about the distal boundary 46, 146 to expose the distal end 30 as described. In the illustrative embodiment shown in FIGS. 19 and 20, the user may grasp the first distal section 42, 142 with the left hand LH and the second distal section 44, 144 with the right hand RH. The clamshell casing 52, 152 is sufficiently opened and the user removes the remainder of the packaging body 22, 122 from the head 36 of the tool 24 with sufficient clearance to avoid contamination. The head 36 of the tool 24 is now exposed and ready for use.

At any point prior to, during, and/or after the surgical procedure, the clamshell casing 52, 152 may be reattached to the tool 24 so as to secure and protect the head 36 of the tool 24 within the clamshell casing 52, 152. In one example, the tool 24 may need to be removed from the surgical device 28 and/or mounted to another surgical device 28. In another example, an intermediate portion of the surgical procedure may not require the tool 24, during which the tool 24 is protected from inadvertent contact and/or contamination. In still another example, an earlier portion of the surgical procedure requiring the tool 24 has been completed, and the tool 24 is protected for the remainder of the procedure, or discarded. Any number of reasons for reattaching the clamshell casing 52, 152 to the tool 24 are contemplated.

Figure 22:
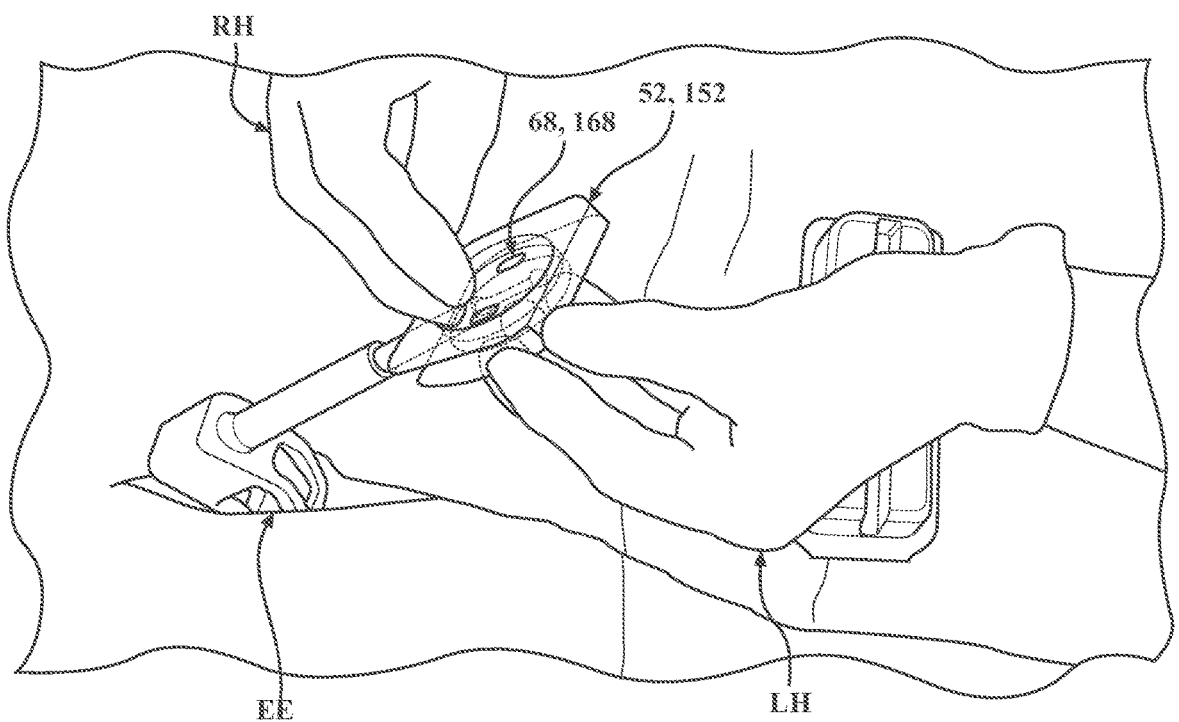
FIG. 22 shows another step of coupling the clamshell casing of the packaging body to the elongate tool.

The method may further include the step of moving the clamshell casing 52, 152 from the second configuration to the first configuration, such as after it had previously been removed from the distal end 30 of the tool 24. The method may further include the step of articulating one of the first distal section 42, 142 and second distal section 44, 144 about the distal boundary 46, 146 relative to the other one of the first distal section 42, 142 and second distal section 44, 144 to prevent exposure of at least a portion of the distal end 30 of the tool 24. With FIGS. 21 and 22 as exemplary, the user supports the first distal section 42, 142 with the left hand LH and the second distal section 44, 144 with the right hand RH. The user moves the clamshell casing 52, 152 proximate the distal end 30 of the tool 24 with the first distal section 42, 142 and the second distal section 44, 144 positioned on opposite sides of the tool 24. The relative articulation between the first distal section 42, 142 and the second distal section 44, 144 is imparted by the user to move the first distal section 42, 142 and the second distal section 44, 144 towards one another. The distal end 30 of the tool 24 is received in one or both of the cavities 54, 56, 154, 156. FIG. 22 shows the user applying a compressive force to the first distal section 42, 142 and the second distal section 44, 144 to engage the couplers 68, 168. The interference fit generated by the engagement of the couplers 68, 168 causes the clamshell casing 52 to securely encase the distal end 30 of the tool 24. The packaging body 22, 122 reassumes the configuration shown in FIG. 18. It is to be understood that the clamshell casing 52, 152 may be decoupled and coupled to the tool 24 as many times as needed prior to, during, and after surgical procedure.

Exemplary methods of assembling the packaging system 20 of the present disclosure are disclosed. The packaging body 22, 122 may be manufactured by thermoforming or another suitable manufacturing process. With reference to FIG. 5, following manufacture the first distal section 42, 142 and second distal section 44, 144 may be positioned in a non-abutting relationship with the primary surface 58, 158 of the second distal section 44, 144 and the primary surface 88, 188 of the proximal section 50, 150 coplanar.

The method further comprises the step of inserting the tool 24 into the packaging body 22, 122. The tool 24 is disposed within the cavity 54, 154 of the first distal section 42, 142 and the cavity 86, 186 of the proximal section 50, 150. More specifically, the distal end 30 of the tool 24, including the head 36, is disposed within the cavity 54, 154 of the first distal section 42, 142, and the shaft 38 of the tool 24, including the proximal end 32, is disposed within the cavity 86, 186 of the proximal section 50, 150. The packaging body 22, 122, assumes the second configuration and the packaging configuration as described. More specifically, the first distal section 42, 142 and second distal section 44, 144 are positioned in a non-abutting relationship, thereby exposing a portion of the distal end 30 of the tool 24, and the proximal end 32 of the tool 24 is disposed within the cavity 86, 186 of the proximal section 50, 150.

The clamshell casing 52, 152 may be moved from the second configuration to the first configuration. The method may further include the step of articulating one of the first distal section 42, 142 and second distal section 44, 144 about the distal boundary 46, 146 relative to the other one of the first distal section 42, 142 and second distal section 44, 144 to prevent exposure at least a portion of the distal end 30 of the tool 24. The packaging body 22, 122, assumes the first configuration shown in FIG. 3. The packaging body 22, 122 remains in the packaging configuration. Secondary packaging 26 may be provided and adapted to receive the packaging body 22, 122. Exemplary methods may comprise disposing the packaging body 22, 122 within the secondary packaging 26.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method for mounting an elongate tool to a surgical device using a segmented packaging body, the elongate tool comprising a distal end and a proximal end, and the segmented packaging body comprising a first distal section, a second distal section pivotably coupled to the first distal section at a first boundary, and a proximal section detachably coupled to the first distal section at a second boundary with said proximal section configured to receive the proximal end of the elongate tool, wherein said segmented packaging body further comprises a perforation at said second boundary configured to facilitate detachment of said first distal section from said proximal section, wherein the first and the second distal sections are removably attached to one another to retain the distal end of the elongate tool within a distal cavity collectively formed by the first and the second distal sections, and the proximal end of the elongate tool is disposed within a proximal cavity formed by the proximal section, wherein each of said first and second distal sections comprise a boss including a slot flanked by ridges with each boss configured to support, within the slot, a shaft of the elongate tool proximal to the distal end to prevent contact between the distal end and said first and second distal sections when the elongate tool is secured within said segmented packaging body, the method comprising:

articulating the proximal section about the second boundary relative to the first distal section for removing the proximal end of the elongate tool from the proximal cavity for exposing the proximal end;

after exposing the proximal end, mounting the proximal end to the surgical device while the distal end remains retained by the first and second distal sections within the distal cavity;

after mounting the proximal end to the surgical device, releasing the distal end of the elongate tool from the distal cavity by:
articulating one of the first and second distal sections about the first boundary relative to the other one of the first and second distal sections for exposing a first portion of the distal end that was retained by the one of the first and second distal sections; and
removing the other one of first and second distal sections from the distal end for exposing a remaining portion of the distal end that was retained by the other one of the first and second distal sections.

2. The method of claim 1, wherein after articulating the proximal section about the second boundary relative to the first distal section, further comprising detaching the proximal section from the first distal section at the second boundary.

3. The method of claim 2, wherein detaching the proximal section from the first distal section at the second boundary further comprises tearing off the proximal section from the first distal section at the perforation.

4. The method of claim 1, wherein the segmented packaging body further comprises couplers for removably attaching the first and second distal sections, wherein articulating one of the first and second distal sections about the first boundary further comprises decoupling the couplers.

5. The method of claim 4, wherein the couplers are provided on the first and second distal sections, and the couplers of one of the first and second distal sections comprise recesses and wherein the couplers of the other one of first and second distal sections comprise protrusions for removably attaching to the recesses by interference fit, and wherein decoupling the couplers further comprises decoupling the recesses and the protrusions from one another.

6. The method of claim 4, wherein the couplers are provided on the first and second distal sections, wherein the couplers of one of the first and second distal sections comprise first and second recesses located on opposite sides of the distal cavity, and wherein the couplers of the other one of first and second distal sections comprise first and second protrusions located on opposite sides of the distal cavity for removably attaching to the first and second recesses by interference fit, and wherein decoupling the couplers further comprises decoupling the first recess and the first protrusion from one another, and decoupling the second recess and the second protrusion from one another.

7. The method of claim 1, wherein the first and second distal sections are removably attached to one another by an interference fit to hold the first and second distal sections together independent of user-applied force, and wherein mounting the proximal end to the surgical device while the distal end remains retained by the first and second distal sections within the distal cavity further comprises grasping the first and second distal sections, that are held together by the interference fit, for moving the proximal end of the elongate tool towards the surgical device.

8. The method of claim 1, wherein articulating one of the first and second distal sections about the first boundary relative to the other one of the first and second distal sections further comprises releasing the first portion of the distal end from a first portion of the distal cavity formed by the one of the first and second distal sections.

9. The method of claim 8, wherein removing the other one of first and second distal sections from the distal end further comprises releasing the remaining portion of the distal end from a remaining portion of the distal cavity formed by the other one of the first and second distal sections.

10. The method of claim 9, wherein after releasing the first portion of the distal end from the first portion of the distal cavity formed by the one of the first and second distal sections, the remaining portion of the distal end remains secured to the other one of the first and second distal sections by the remaining portion of the distal cavity.

11. The method of claim 1, wherein the distal end of the elongate tool is a curved bur and the distal cavity is contoured to the curved bur to capture the curved bur such that the curved bur is irremovable from the distal cavity when the first and second distal sections are attached to one another, and wherein releasing the distal end of the elongate tool from the distal cavity further comprises releasing the curved bur from the distal cavity by:
 articulating one of the first and second distal sections about the first boundary relative to the other one of the first and second distal sections for exposing the first portion of the curved bur that was retained by a first contoured portion of the distal cavity formed by the one of the first and second distal sections; and
 removing the other one of first and second distal sections from the curved bur for exposing the remaining portion of the curved bur that was retained by a remaining contoured portion of the distal cavity formed by the other one of the first and second distal sections.

12. The method of claim 1, wherein the proximal section comprises first and second side walls that extend along the tool shaft to capture opposing sides of the tool shaft, and an end wall that is coupled to each of the first and second side walls and that is oriented perpendicular to the tool shaft, and wherein the proximal cavity is formed by the first and second side walls and the end wall, and wherein the proximal end of the elongate tool comprises a proximal face that faces the end wall within the proximal cavity, and wherein articulating the proximal section about the second boundary relative to the first distal section further comprises articulating the proximal section for removing the proximal end of the elongate tool from the proximal cavity for exposing the proximal face of the proximal end.

13. A method for mounting an elongate tool to a surgical device using a segmented packaging body, the elongate tool comprising a distal end and a proximal end, and the segmented packaging body comprising a first distal section, a second distal section pivotably coupled to the first distal section at a first boundary, and a proximal section pivotably coupled to the first distal section at a second boundary, wherein the first and the second distal sections are removably attached to one another to retain the distal end of the elongate tool within a distal cavity collectively formed by the first and the second distal sections, and the proximal end of the elongate tool is disposed within a proximal cavity formed by the proximal section, the method comprising:
 articulating the proximal section about the second boundary relative to the first distal section for removing the proximal end of the elongate tool from the proximal cavity for exposing the proximal end;
 after exposing the proximal end, mounting the proximal end to the surgical device while the distal end remains retained by the first and second distal sections within the distal cavity;
 after mounting the proximal end to the surgical device, releasing the distal end of the elongate tool from the distal cavity by:
  articulating one of the first and second distal sections about the first boundary relative to the other one of the first and second distal sections for exposing a first portion of the distal end that was retained by the one of the first and second distal sections; and
 removing the other one of first and second distal sections from the distal end for exposing a remaining portion of the distal end that was retained by the other one of the first and second distal sections,
 wherein the elongate tool comprises a tool shaft and wherein the proximal section comprises first and second side walls that extend along the tool shaft to capture opposing sides of the tool shaft, and wherein that the proximal cavity is formed, at least in part, by the first and second side walls, and wherein at least one of the side walls further defines a recess that extends away from the tool shaft to define a separation region between the tool shaft and the at least one of the side walls to enable grasping of the tool shaft in the separation region within the proximal cavity, and wherein articulating the proximal section about the second boundary relative to the first distal section further comprises grasping the tool shaft in the separation region for articulating the proximal section relative to the tool shaft.

* * * * *